(12) United States Patent
Zhang et al.

(10) Patent No.: US 11,596,446 B2
(45) Date of Patent: Mar. 7, 2023

(54) HINGE-LINK SPINAL CORRECTION DEVICE AND METHOD

(71) Applicant: Texas Scottish Rite Hospital for Children, Dallas, TX (US)

(72) Inventors: Hong Zhang, Plano, TX (US); John David Ross, Jr., Ovilla, TX (US); Daniel J. Sucato, Dallas, TX (US)

(73) Assignee: Texas Scottish Rite Hospital for Children, Dallas, TX (US)

( * ) Notice: Subject to any disclaimer, the term of this patent is extended or adjusted under 35 U.S.C. 154(b) by 0 days.

(21) Appl. No.: 16/820,097

(22) Filed: Mar. 16, 2020

(65) Prior Publication Data

US 2020/0297390 A1 Sep. 24, 2020

Related U.S. Application Data

(60) Provisional application No. 62/822,345, filed on Mar. 22, 2019.

(51) Int. Cl.
*A61B 17/70* (2006.01)
*A61B 17/88* (2006.01)

(52) U.S. Cl.
CPC ...... *A61B 17/7023* (2013.01); *A61B 17/7049* (2013.01)

(58) Field of Classification Search
CPC ............ A61B 17/7023; A61B 17/7019; A61B 17/7049; A61B 17/705; A61B 17/7052
USPC ....... 606/256, 250, 251, 253, 257, 259, 266, 606/278, 279
See application file for complete search history.

(56) References Cited

U.S. PATENT DOCUMENTS

| | | | |
|---|---|---|---|
| 4,361,141 A * | 11/1982 | Tanner | A61B 17/7052 606/252 |
| 6,755,828 B2 | 6/2004 | Shevtsov et al. | |
| 7,455,685 B2 | 11/2008 | Justis | |
| 8,016,861 B2 | 9/2011 | Mitchell et al. | |
| 8,147,519 B2 * | 4/2012 | Wilcox | A61B 17/705 606/260 |
| 9,433,433 B2 | 9/2016 | Montello et al. | |

(Continued)

FOREIGN PATENT DOCUMENTS

| | | |
|---|---|---|
| CN | 102499741 B | 12/2013 |
| WO | 2012074803 A1 | 6/2012 |

*Primary Examiner* — Eduardo C Robert
*Assistant Examiner* — David C Comstock
(74) *Attorney, Agent, or Firm* — Edwin S. Flores; Chalker Flores, LLP

(57) ABSTRACT

A device for spinal correction includes a stabilizer assembly including a hinge including a first rod-bearing leaf; a second rod-bearing leaf rotatably coupled to the first rod-bearing leaf to provide coronal or sagittal freedom of movement, or both, of the stabilizer assembly; a locking mechanism to lock the first and second rod-bearing leaves at a desired angle; a first stabilizing rod coupled to the first rod-bearing leaf; a second stabilizing rod coupled to the second rod-bearing leaf; and a plurality of monoaxial or polyaxial links, wherein each monoaxial or polyaxial link is movably coupled to the first or second stabilizing rod and is movably couplable to a first spinal rod or a second spinal rod fixed to the spine; wherein the stabilizer assembly is couplable to the first or second spinal rod to stabilize the spine to prevent compression, distraction, or translation of the spinal cord during a spinal correction.

21 Claims, 36 Drawing Sheets

(56) References Cited

U.S. PATENT DOCUMENTS

| | | | |
|---|---|---|---|
| 9,579,126 B2* | 2/2017 | Zhang | A61B 17/705 |
| 10,004,538 B2 | 6/2018 | McNab et al. | |
| 10,105,166 B2 | 10/2018 | Zhang et al. | |
| 2006/0229611 A1* | 10/2006 | Avery | A61B 17/7055 |
| | | | 606/260 |
| 2008/0033434 A1* | 2/2008 | Boomer | A61B 17/7013 |
| | | | 606/264 |
| 2008/0234743 A1* | 9/2008 | Marik | A61B 17/705 |
| | | | 606/257 |
| 2009/0093847 A1* | 4/2009 | Wilcox | A61B 17/705 |
| | | | 606/259 |
| 2017/0056074 A1 | 3/2017 | Zhang et al. | |

* cited by examiner

HINGE-LINK SPINAL CORRECTION DEVICE AND METHOD

CROSS-REFERENCE TO RELATED APPLICATIONS

This application is a non-provisional patent application of and claims priority to U.S. provisional patent application Ser. No. 62/822,345 filed on Mar. 22, 2019 and entitled "Hinge-Link Spinal Correction Device and Method," the contents of which are hereby incorporated by reference in their entirety.

STATEMENT OF FEDERALLY FUNDED RESEARCH

Not applicable.

TECHNICAL FIELD OF THE INVENTION

The present invention relates in general to the treatment of spinal deformations. In particular, the present invention relates to the correction of spinal deformation in which a vertebral column resection is performed.

BACKGROUND OF THE INVENTION

Without limiting the scope of the invention, its background is described in connection with the use of a device to stabilize and manipulate a deformed spine on which a vertebral column resection (VCR) or spinal correction is being or has been performed into a desired position and then fixing the spine in that configuration. In some cases of severe spinal deformity, it is advisable to remove one or more vertebrae to allow manipulation of the spine into a more normal curve, sometimes in stages over a period of time. The spine must be stabilized for performance of the VCR; manipulated into the more normal configuration; held in place over a period of time until the spine adapts to that configuration, and sometimes stabilized and manipulated repeatedly during subsequent spinal corrections and then held in place until the spine adapts to each new configuration. Prior art method and systems are difficult and risky because they do not provide for fine control of the initial stabilization during the VCR, stabilization, manipulation, or the long-term fixing in place of the spine without risk of compression, distraction, or translation of the spinal cord.

U.S. Pat. No. 9,433,433, to Montello, et al., is said to disclose a posterior vertebral plating system comprising a plate and a plurality of attachment members. The plate is said to have a plurality of holes extending through the plate from an upper surface to a lower surface, and the plate is configured to extend along the posterior side of at least two vertebrae adjacent at least one boney structure of each of the vertebrae. The holes are said to be spaced in such a way that a first plurality of holes is positionable over a boney structure of a first vertebra to define a plurality of fixation points to the first vertebra and a second plurality of holes is positionable over boney structure of a second vertebra to define a plurality of fixation points to the second vertebra. The attachment members are said to be insertable through the holes of the plate and into the boney structure of a corresponding vertebra to fix the plate to the vertebra.

U.S. Pat. No. 10,004,538, to McNab et al., is said to disclose a surgical instrument that includes a first arm engageable with a first spinal construct disposed with a first vertebral surface. A second arm is said to be connected with the first arm via a pivot and to be engageable with a second spinal construct disposed with a second vertebral surface. The first arm is said to be movable to rotate the first spinal construct relative to the pivot and/or the second arm is said to be movable to rotate the second spinal construct relative to the pivot such that the first vertebral surface is moved relative to the second vertebral surface.

U.S. Pat. No. 9,579,126, to Zhang, et al., and U.S. Pat. No. 10,105,166, to Zhang, et al., are said to disclose a rod link reducer of a spinal fixation system that includes a first and a second spinal rod manipulator; a first spinal rod manipulator joint connected to the first spinal rod manipulator and a second spinal rod manipulator joint connected to the second spinal rod manipulator; a first and a second translatable transverse shaft connected to the first and second joints, respectively; and a universal reducer connected to both the first and second translatable transverse shafts, wherein the universal reducer, the shafts and the linkers provide movement and temporary fixation of a spine that has been manipulated into a final position during spinal surgery.

Methods and systems for stabilization, manipulation, and fixation of a deformed spine subject to a VCR are ineffective and risky. Effective methods and systems that reduce risk for stabilization, manipulation, and fixation of a deformed spine subject to a VCR to prevent compression, distraction, or translation of the spinal cord are desirable.

SUMMARY OF THE INVENTION

In some embodiments of the disclosure, a device for spinal correction is disclosed as including a stabilizer assembly including: a hinge including: a first rod-bearing leaf; a second rod-bearing leaf rotatably coupled to the first rod-bearing leaf to provide coronal or sagittal freedom of movement, or both, of the stabilizer assembly; a locking mechanism to lock the first rod-bearing leaf and the second rod-bearing leaf at a desired angle; a first stabilizing rod coupled to the first rod-bearing leaf; a second stabilizing rod coupled to the second rod-bearing leaf; and a plurality of monoaxial or polyaxial links, wherein each monoaxial or polyaxial link is movably coupled to the first stabilizing rod or to the second stabilizing rod and is movably couplable to a first spinal rod fixed to a spine or to a second spinal rod fixed to the spine; wherein the stabilizer assembly is couplable to the first spinal rod or to the second spinal rod to stabilize the spine to prevent compression, distraction, or translation of the spinal cord during a spinal correction. In one aspect, the locking mechanism to lock the first rod-bearing leaf and the second rod-bearing leaf at the desired angle includes one or more screws. In another aspect, the first stabilizing rod is coupled to the first rod-bearing leaf with a first threaded portion of the first stabilizing rod. In another aspect, the second stabilizing rod is coupled to the second rod-bearing leaf with a second threaded portion of the second stabilizing rod. In another aspect, each monoaxial or polyaxial link is movably coupled to the first stabilizing rod or to the second stabilizing rod with one or more adjustment nuts or one or more locking pins. In another aspect, each polyaxial link is lockable at a position on the first stabilizing rod or the second stabilizing rod and is lockable at an angle to the first stabilizing rod or the second stabilizing rod with two or more adjustment nuts. In another aspect, each monoaxial or polyaxial link is movably couplable to the first spinal rod or to the second spinal rod at one or more components, each comprising a recess shaped to receive the first spinal rod or to the second spinal rod, and lockable in position with one or more screws. In another aspect, the first stabilizing rod is rotatably coupled to the first rod-bearing leaf to provide coronal or sagittal freedom of movement, or both, of the first stabilizing rod or the second stabilizing rod is rotatably coupled to the second rod-bearing leaf to provide coronal or sagittal freedom of movement, or both, of the second stabilizing rod; and the first stabilizing rod has a locking mechanism to lock it at a desired position or the second stabilizing rod has a locking mechanism to lock it at a desired position. In another aspect, the first stabilizing rod or the second stabilizing rod is threaded and adjustment nuts are mounted on the first stabilizing rod or the second stabilizing rod to provide longitudinal freedom of movement or locking of one or more of the plurality of monoaxial or polyaxial links on the first stabilizing rod or the second stabilizing rod.

In some embodiments of the disclosure, a kit is disclosed as including a stabilizer assembly including: a hinge including: a first rod-bearing leaf; a second rod-bearing leaf rotatably coupled to the first rod-bearing leaf to provide coronal or sagittal freedom of movement, or both, of the stabilizer assembly; a locking mechanism to lock the first rod-bearing leaf and the second rod-bearing leaf at a desired angle; a first stabilizing rod coupled to the first rod-bearing leaf; a second stabilizing rod coupled to the second rod-bearing leaf; and a plurality of monoaxial or polyaxial links, wherein each monoaxial or polyaxial link is movably coupled to the first stabilizing rod or to the second stabilizing rod and is movably couplable to a first spinal rod fixed to a spine or to a second spinal rod fixed to the spine; wherein the stabilizer assembly is couplable to the first spinal rod or to the second spinal rod to stabilize the spine to prevent compression, distraction, or translation of the spinal cord during a spinal correction. In one aspect, the first stabilizing rod is rotatably coupled to the first rod-bearing leaf to provide coronal or sagittal freedom of movement, or both, of the first stabilizing rod or the second stabilizing rod is rotatably coupled to the second rod-bearing leaf to provide coronal or sagittal freedom of movement, or both, of the second stabilizing rod; and the first stabilizing rod has a locking mechanism to lock it at a desired position or the second stabilizing rod has a locking mechanism to lock it at a desired position. In another aspect, the first stabilizing rod or the second stabilizing rod is threaded and adjustment nuts are mounted on the first stabilizing rod or the second stabilizing rod to provide longitudinal freedom of movement or locking of one or more of the plurality of monoaxial or polyaxial links on the first stabilizing rod or the second stabilizing rod.

In some embodiments of the disclosure, a method of stabilizing a spine is disclosed as including providing a patient in need of stabilization of a spine, wherein a plurality of spinal rods have been fixed to the spine; coupling a stabilizer assembly of a device for spinal correction to at least one of the plurality of spinal rods, wherein the stabilizer assembly includes: a hinge including: a first rod-bearing leaf; a second rod-bearing leaf rotatably coupled to the first rod-bearing leaf to provide coronal or sagittal freedom of movement, or both, of the stabilizer assembly; and a locking mechanism to lock the first rod-bearing leaf and the second rod-bearing leaf at a desired angle; a first stabilizing rod coupled to the first rod-bearing leaf; a second stabilizing rod coupled to the second rod-bearing leaf; and a plurality of monoaxial or polyaxial links, wherein each monoaxial or polyaxial link is movably coupled to the first stabilizing rod or to the second stabilizing rod and is movably coupled to a first spinal rod fixed to a spine or to a second spinal rod fixed to the spine; and stabilizing the spine at a desired spinal configuration; wherein the stabilizer assembly is couplable to the first spinal rod or to the second spinal rod to stabilize the spine to prevent compression, distraction, or translation of the spinal cord during a spinal correction. In one aspect, the locking mechanism to lock the first rod-bearing leaf and the second rod-bearing leaf at the desired angle includes one or more screws. In another aspect, the first stabilizing rod is coupled to the first rod-bearing leaf with a first threaded portion of the first stabilizing rod. In another aspect, the second stabilizing rod is coupled to the second rod-bearing leaf with a second threaded portion of the second stabilizing rod. In another aspect, each monoaxial or polyaxial link is movably coupled to the first stabilizing rod or to the second stabilizing rod with one or more adjustment nuts or one or more locking pins. In another aspect, each polyaxial link is lockable at a position on the first stabilizing rod or the second stabilizing rod and is lockable at an angle to the first stabilizing rod or the second stabilizing rod with two or more adjustment nuts. In another aspect, each monoaxial or polyaxial link is movably couplable to the first spinal rod or to the second spinal rod at one or more components, each comprising a recess shaped to receive the first spinal rod or to the second spinal rod, and lockable in position with one or more screws. In another aspect, the first stabilizing rod is rotatably coupled to the first rod-bearing leaf to provide coronal or sagittal freedom of movement, or both, of the first stabilizing rod or the second stabilizing rod is rotatably coupled to the second rod-bearing leaf to provide coronal or sagittal freedom of movement, or both, of the second stabilizing rod; and the first stabilizing rod has a locking mechanism to lock it at a desired position or the second stabilizing rod has a locking mechanism to lock it at a desired position. In another aspect, the first stabilizing rod or the second stabilizing rod is threaded and adjustment nuts are mounted on the first stabilizing rod or the second stabilizing rod to provide longitudinal freedom of movement or locking of one or more of the plurality of monoaxial or polyaxial links on the first stabilizing rod or the second stabilizing rod. In another aspect, the first stabilizing rod or the second stabilizing rod is threaded and adjustment nuts are mounted on the first stabilizing rod or the second stabilizing rod to provide longitudinal freedom of movement or locking of one or more of the plurality of monoaxial or polyaxial links on the first stabilizing rod or the second stabilizing rod. In another aspect, the method further includes coupling the stabilizer assembly to at least one of the plurality of spinal rods oriented to allow the hinge to have coronal freedom of movement, sagittal freedom of movement, or a combination of coronal and sagittal freedom of movement.

BRIEF DESCRIPTION OF THE DRAWINGS

For a more complete understanding of the features and advantages of the present invention, reference is now made to the detailed description of the invention along with the accompanying figures, in which:

FIG. 2I shows a lateral view of the stabilizer assembly of FIG. 2A.

DETAILED DESCRIPTION OF THE INVENTION

Illustrative embodiments of the system of the present application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

Figure 1A:
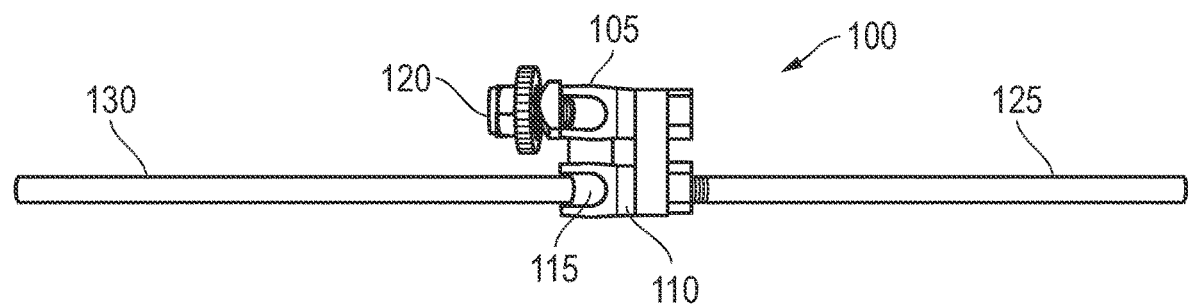
FIGS. 1A, 1B, and 1C show a stabilizer assembly.
Figure 1B:
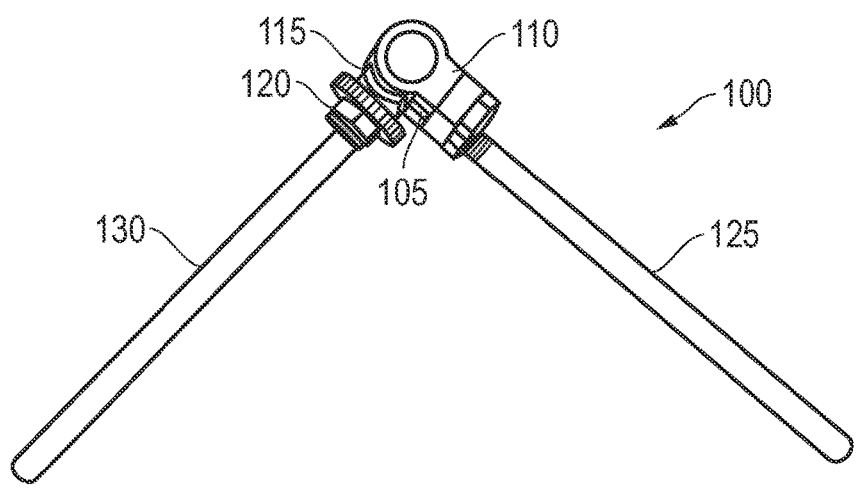

FIGS. 1A and 1B show an embodiment of the present invention which prevents compression, distraction, or translation of the spinal cord during a vertebral resection surgery, the stabilizer assembly 100. FIG. 1A shows a side view and FIG. 1B shows a top view. The stabilizer assembly 100 includes the hinge 105, which includes rod-bearing leaves 110 and 115 and hinge locking mechanism 120. The rod-bearing leaf 115 is rotatably coupled to the rod-bearing leaf 110 to allow coronal or sagittal freedom of movement, or both, depending on the orientation of the stabilizer assembly relative to the spine. Hinge locking mechanism 120 is used to lock the rod-bearing leaves 110 and 115 at a desired angle. Stabilizing rods 125 and 130 are coupled to the rod-bearing leaves 110 and 115, via, e.g., threaded portions of the stabilizing rods 125 and 130 nearest the hinge 105. The stabilizing rod 125, the stabilizing rod 130, or both are threaded and adjustment nuts are mounted on the stabilizing rod 125, the stabilizing rod 130, or both to provide longitudinal freedom of movement.

Figure 1C:
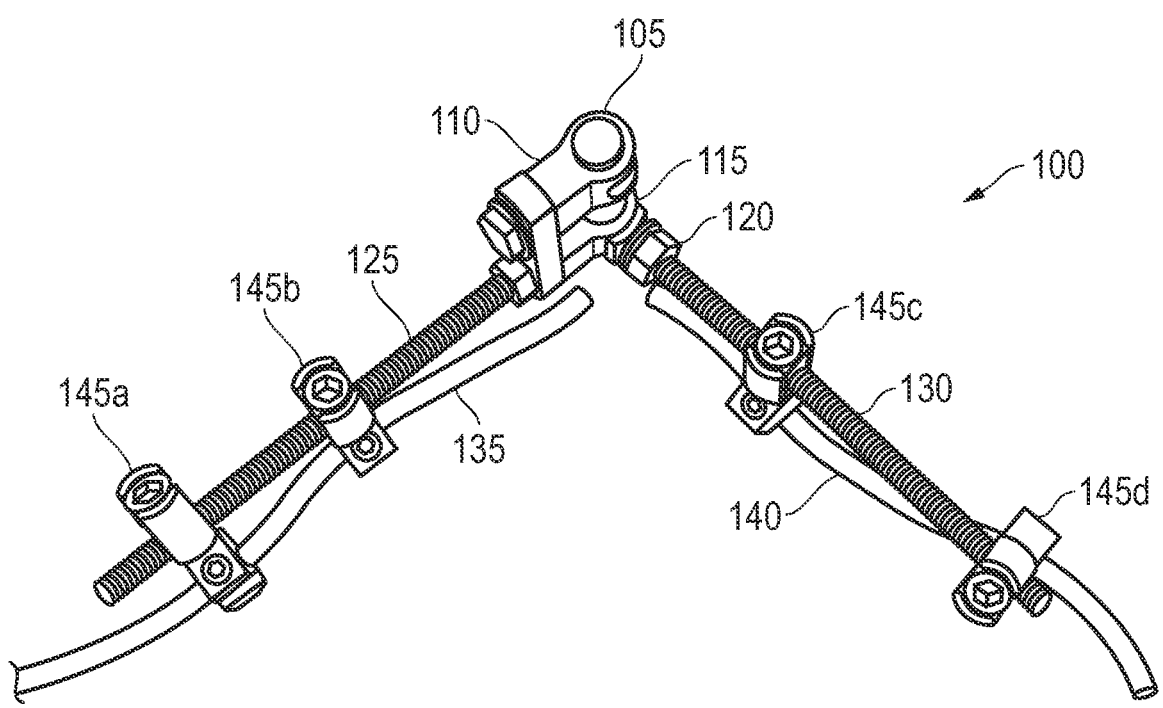

FIG. 1C shows the stabilizer assembly 100 of the present invention coupled to the spinal rods 135 and 140, which may be straight or curved. FIG. 1C shows the hinge 105 with the rod-bearing leaves 110 and 115, the locking mechanism 120, the stabilizing rods 125 and 130, and four links 145a, 145b, 145c, and 145d. The links 145a, 145b, 145c, and 145d are coupled to the spinal rods 135 and 140. The links 145a, 145b, 145c, and 145d represent a number of embodiments of links of the present invention, including monoaxial and polyaxial links described herein.

Figure 2A:
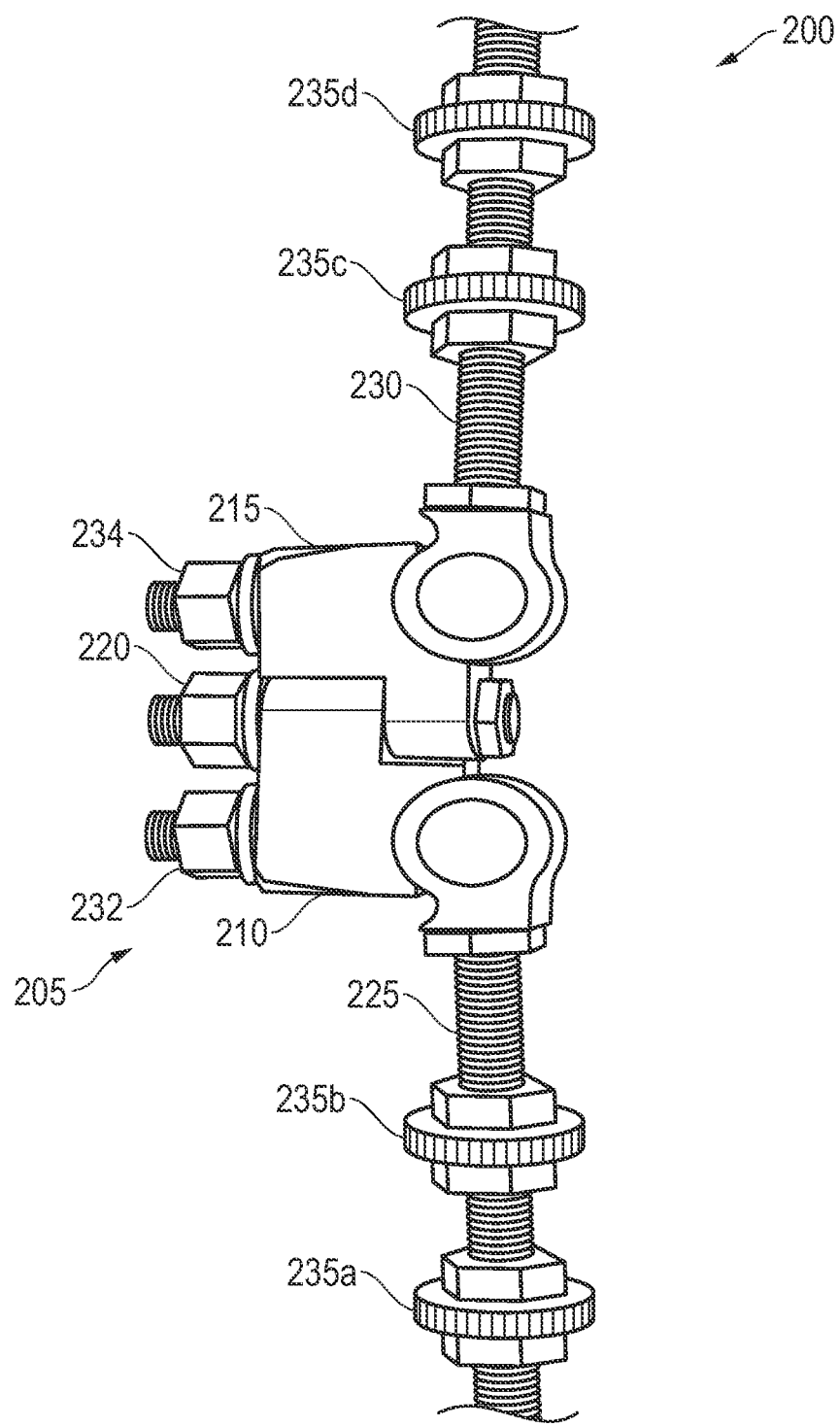
FIG. 2A shows another stabilizer assembly.

FIG. 2A depicts another embodiment of the present invention which prevents compression, distraction, or translation of the spinal cord during a vertebral resection surgery, the stabilizer assembly 200. The stabilizer assembly includes the hinge 205, which is configured to allow coronal or sagittal freedom of movement, or both, of the stabilizer assembly, depending on the orientation of the stabilizer assembly relative to the spine. Rod-bearing leaves 210 and 215 are rotatably coupled to allow coronal or sagittal freedom of movement, or both, depending on the orientation of the stabilizer assembly relative to the spine. Hinge locking mechanism 220 is used to lock the rod-bearing leaves 210 and 215 at a desired angle. Stabilizing rods 225 and 230, which are threaded on at least a portion of their respective lengths, are coupled to the rod-bearing leaves 210 and 215, via, e.g., threaded portions at the ends of the stabilizing rods 225 and 230 nearest the hinge 205. The stabilizing rods 225 and 230 are rotatably coupled to the rod-bearing leaves 210 and 215 such that they have freedom of movement with axes of rotation that are at right angles to a plane formed when the rod-bearing leaves 210 and 215 form a 180-degree angle. Locking mechanisms 232 and 234 are used to lock the stabilizing rods 225 and 230, respectively, at desired positions. The stabilizing rods 225 and 230 are threaded and carry exemplary adjustment nuts 235a, 235b, 235c, and 235d to move links (not shown) longitudinally on the stabilizing rods 225 and 230, allowing longitudinal freedom of movement along the stabilizing rods 225 and 230. The adjustment nuts 235a, 235b, 235c, and 235d can be used to lock links in place on the stabilizing rods 225 and 230.

Figure 2B:
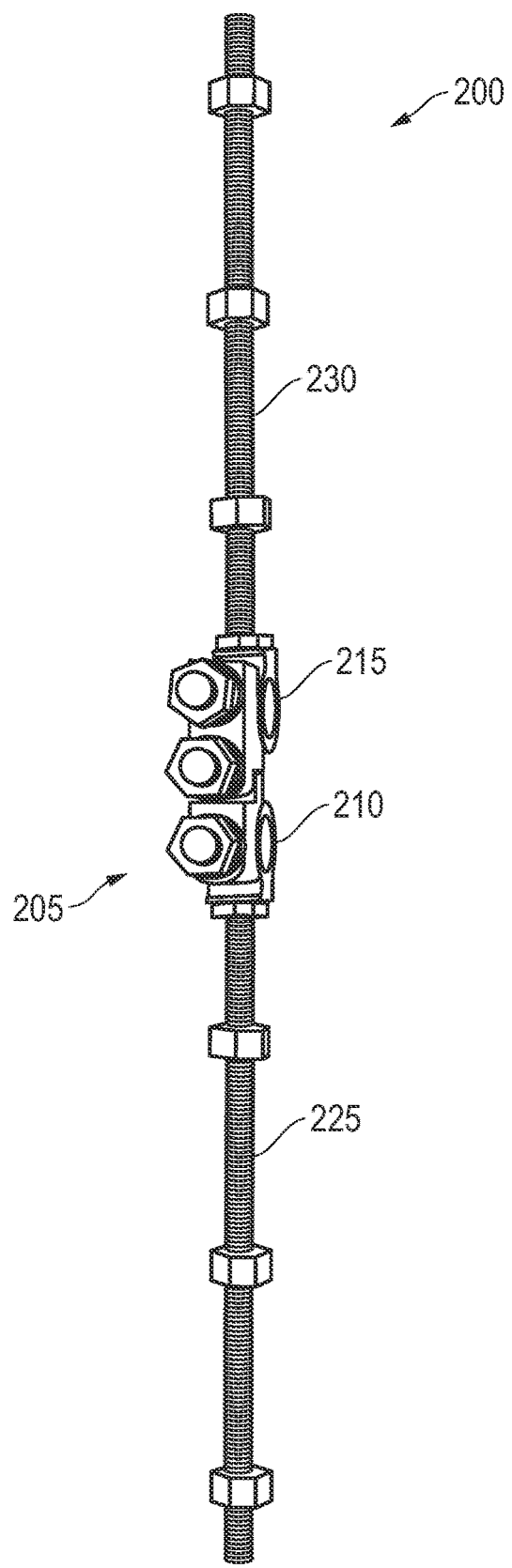
FIGS. 2B, 2C, and 2D illustrate top views of the stabilizer assembly of FIG. 2A.
Figure 2C:
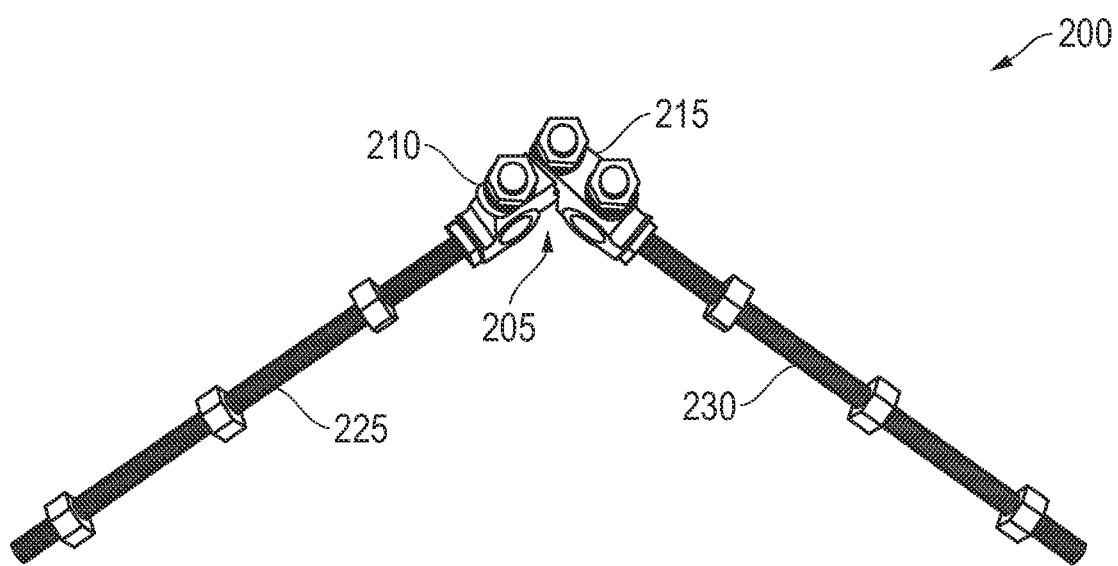
Figure 2D:
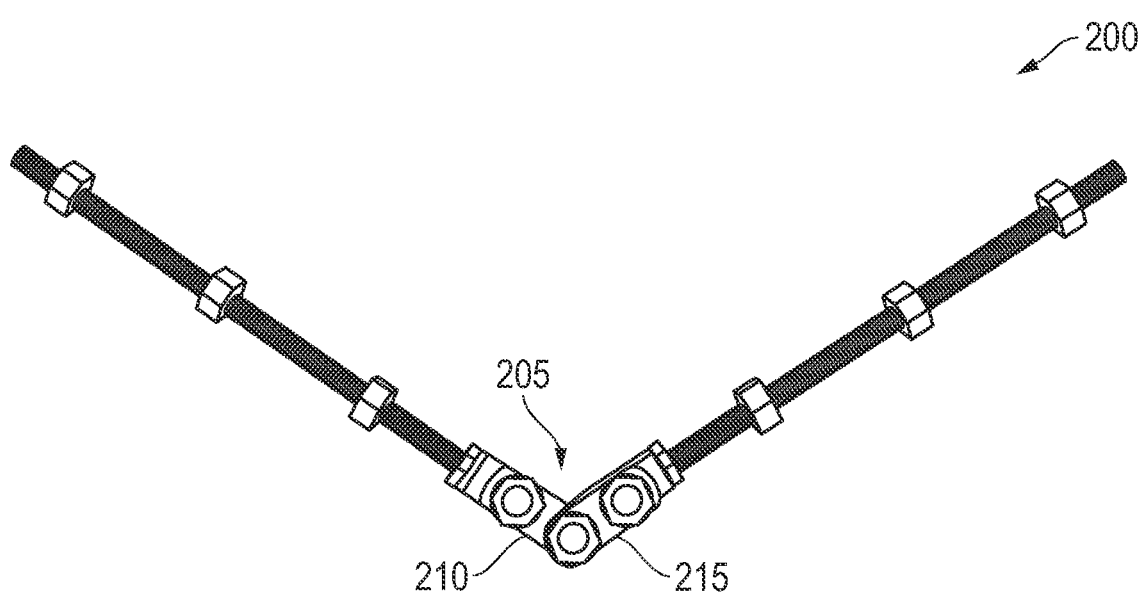

FIG. 2B shows a top view of the stabilizer assembly 200 with the rod-bearing leaves 210 and 215 of the hinge 205 set at a 180-degree angle. FIGS. 2C and 2D depict top views of the stabilizer assembly 200 with the rod-bearing leaves 210 and 215 of the hinge 205 set at different angles to provide examples of the coronal freedom of motion allowed by the hinge 205.

Figure 2E:
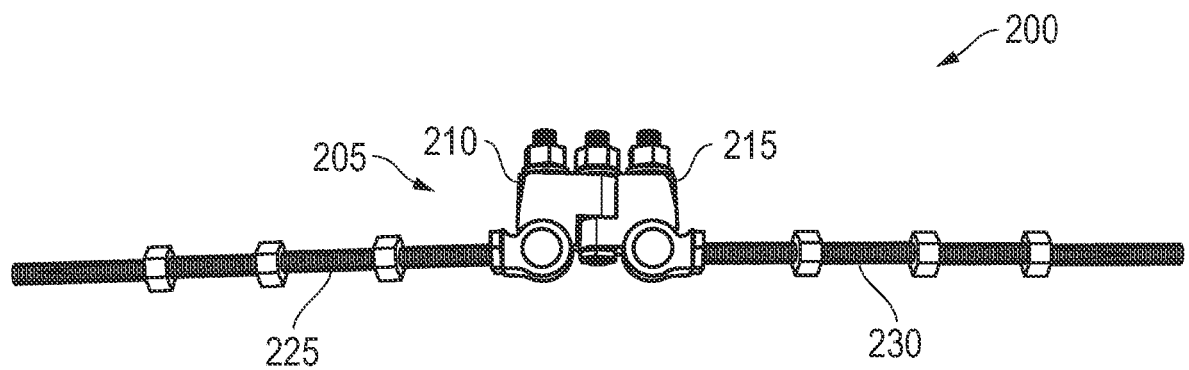
FIGS. 2E, 2F, and 2G illustrate perspective views of the stabilizer assembly of FIG. 2A.
Figure 2F:
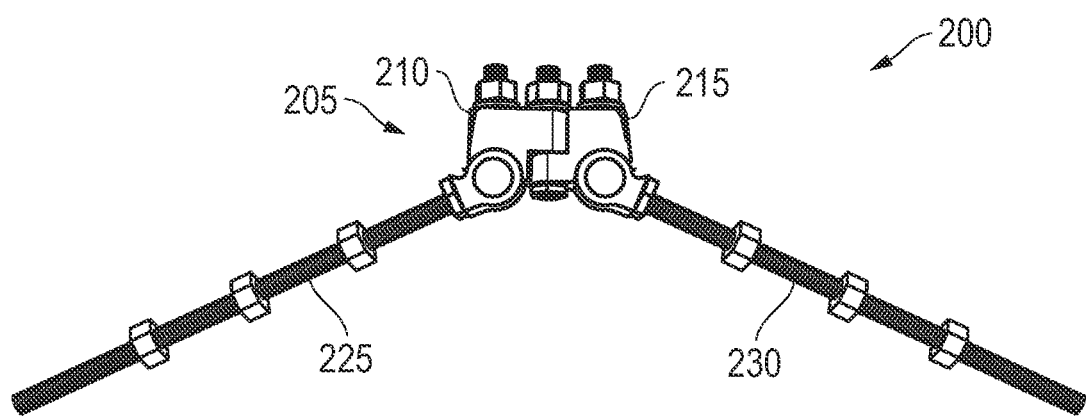
Figure 2G:
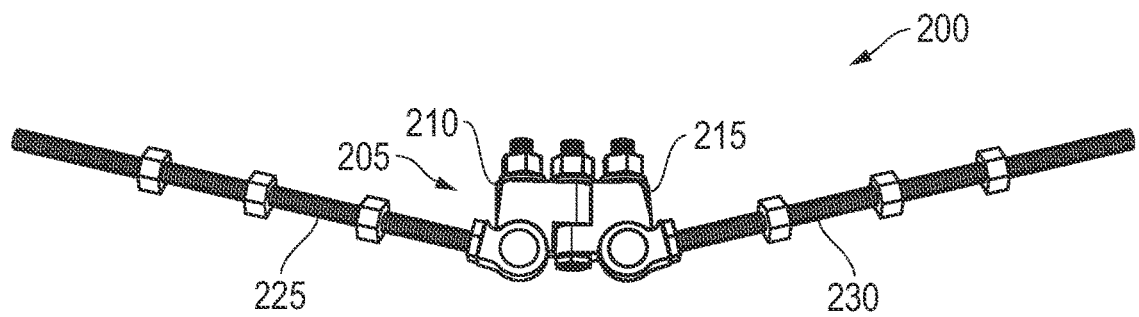

FIG. 2E shows a lateral view of the stabilizer assembly 200 with the rod-bearing leaves 210 and 215 of the hinge 205 set at a 180-degree angle and the stabilizing rods 225 and 230 aligned with each other. FIGS. 2F and 2G depict lateral views of the stabilizer assembly 200 with the rod-bearing leaves 210 and 215 of the hinge 205 set a 180-degree angle and the stabilizing rods 225 and 230 set at different angles to provide examples of the sagittal freedom of motion of the stabilizing rods 225 and 230.

Figure 2H:
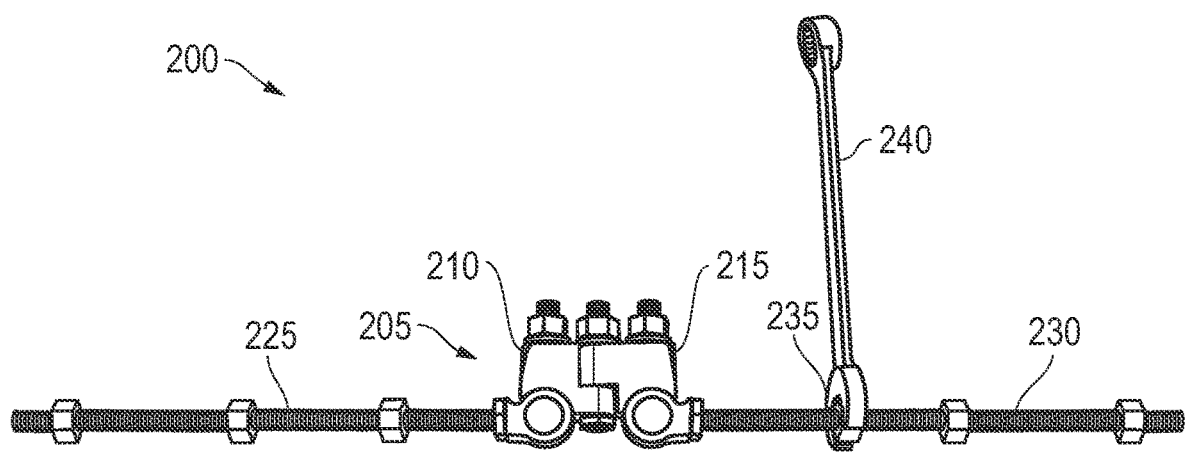
FIG. 2H depicts a view of the stabilizer assembly of FIG. 2A with a wrench to adjust adjustment nuts.
Figure 21:
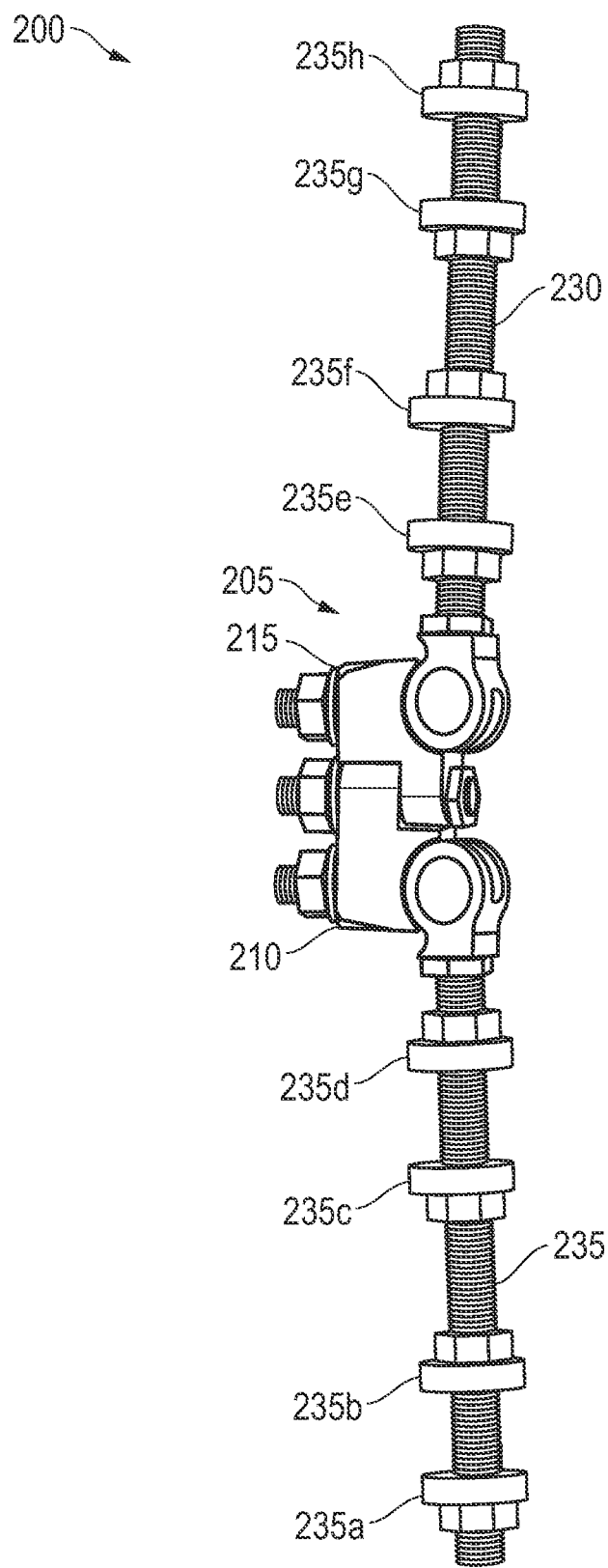

FIG. 2H shows a lateral view of the stabilizer assembly 200 with the rod-bearing leaves 210 and 215 of the hinge 205 set at a 180-degree angle and the stabilizing rods 225 and 230 aligned with each other, with a wrench 240 positioned to adjust an adjustment nut 235 to move it longitudinally on the stabilizing rod 230 to position a link (not shown) on the stabilizing rod 230.

FIG. 2I shows a lateral view of the stabilizer assembly 200 with the rod-bearing leaves 210 and 215 of the hinge 205 set at a 180-degree angle and the stabilizing rods 225 and 230 aligned with each other, with eight exemplary adjustment nuts 235a, 235b, 235c, 235d, 235e, 235f, 235g, and 235h, four on each of the stabilizing rods 225 and 230. The adjustment nuts can be made from any material such as metal, polymers, composites, etc.

Figure 3A:
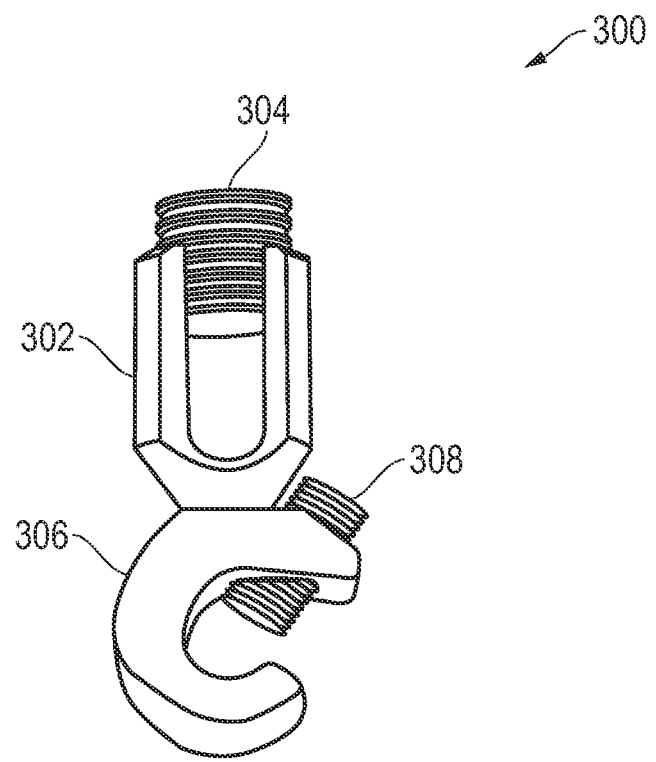
FIG. 3A shows a monoaxial link.

FIG. 3A shows a monoaxial link 300 of the present invention. FIG. 3A illustrates a monoaxial link 300 of the present invention. A plurality of links 300 may be movably coupled to one or both of the stabilizing rods 125 and 130 (not shown), at the upper end 302 of each link 300. Each link 300 can be positioned as desired on a stabilizing rod 125 or 130 using, e.g, a set-screw 304, to lock it into position. Each link 300 is movably couplable to a spinal rod (not shown) that is fixed to a spine using, e.g., bone screws, at the lower end 306 of each link 300. Each link 300 can be positioned as desired on spinal rod using, e.g, a set-screw 308, to lock it into position.

Figure 3B:
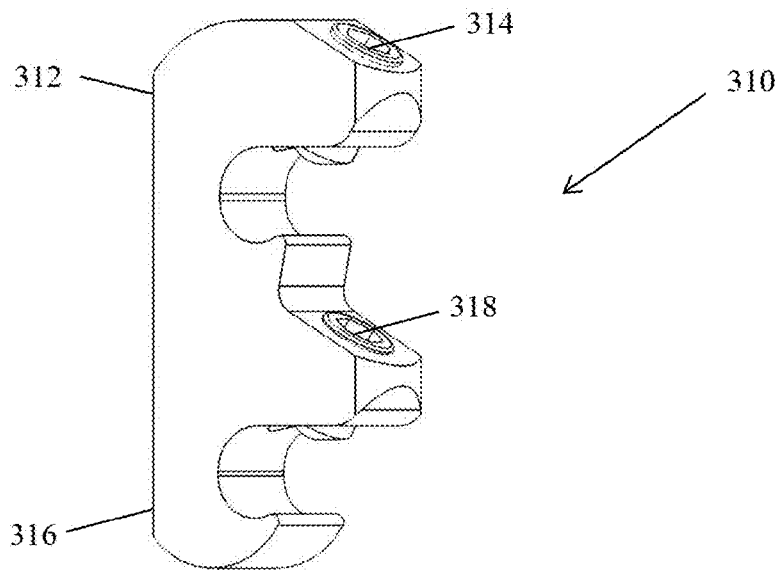
FIG. 3B shows another monoaxial link.

FIG. 3B illustrates another monoaxial link 310 of the present invention. A plurality of links 310 may be movably coupled to one or both of the stabilizing rods 125 and 130 (not shown), at the upper end 312 of each link 310. Each link 310 can be positioned as desired on a stabilizing rod 125 or 130 using, e.g, a set-screw 314, to lock it into position. Each link 310 is movably couplable to a spinal rod (not shown) that is fixed to a spine using, e.g., bone screws, at the lower end 316 of each link 310. Each link 310 can be positioned as desired on spinal rod using, e.g, a set-screw 318, to lock it into position.

Figure 3C:
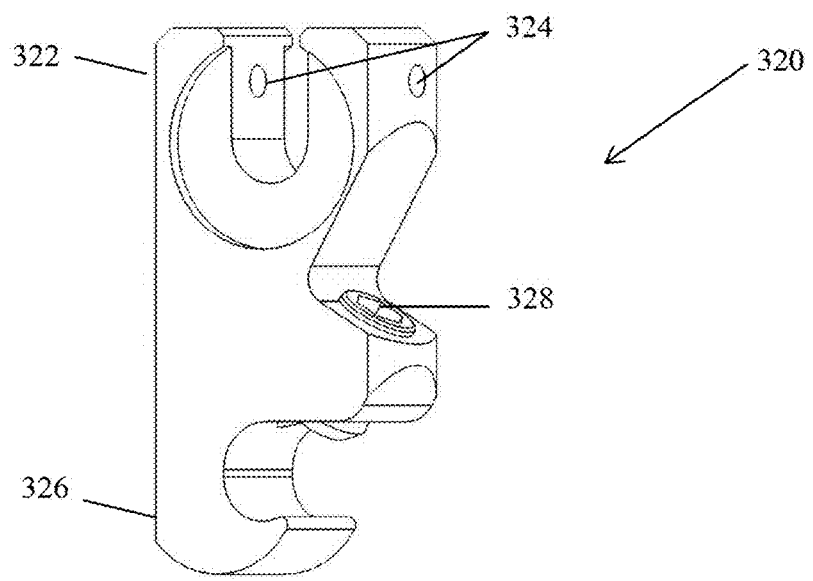
FIG. 3C shows still another monoaxial link.

FIG. 3C illustrates still another monoaxial link 320 of the present invention. A plurality of links 320 may be movably coupled to one or both of the stabilizing rods 125 and 130 (not shown), at the upper end 322 of each link 320. Each link 320 can be positioned as desired on a stabilizing rod 125 or 130 using, e.g, a locking pin (not shown) set in place through holes 324, to retain the link 320 on the stabilizing rod 125 or 130 (not shown). Each link 320 is movably couplable to a spinal rod (not shown) that is fixed to a spine using, e.g., bone screws, at the lower end 326 of each link 320. Each link 320 can be positioned as desired on spinal rod using, e.g, a set-screw 328, to lock it into position.

Figure 3D:
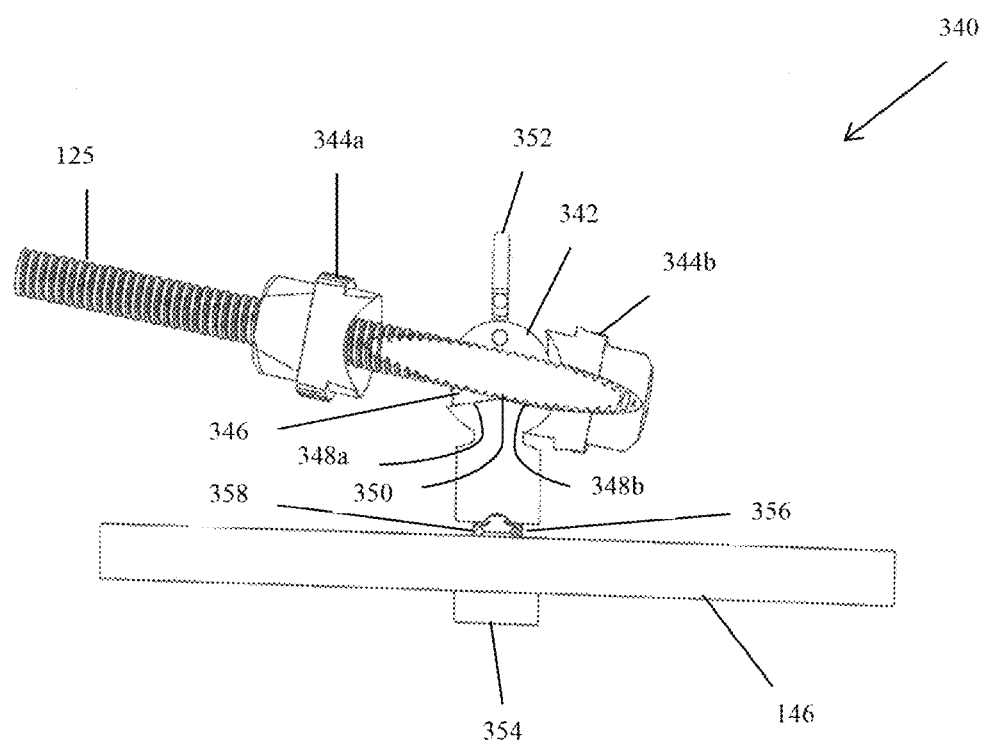
FIG. 3D shows a cross-section of a polyaxial link.

FIG. 3D shows a cross-section, and FIGS. 3E, 3F, 3G, and 3H show perspective views of a polyaxial link 340 of the present invention, with each figure showing one or more features of the polyaxial link 340 in various configurations. Each of a plurality of polyaxial links 340 is movably coupled to one of the stabilizing rods 125 and 130 (of which stabilizing rod 125 is shown and stabilizing rod 130 is not shown), at the upper portion 342 of each polyaxial link 340. Each polyaxial link 340 can be positioned as desired on a stabilizing rod 125 or 130 (130 not shown) using e.g., a pair of adjustment nuts 344a and 344b, shaped to match the shape of the upper portion 342, to lock it into position. These adjustment nuts 344a and 344b, and similar ones elsewhere on the threaded stabilizing rod 125 or 130 (130 not shown), can be locked and unlocked multiple times without damaging the adjustment nut threads or the stabilizing rod threads. The upper portion 342 of polyaxial link 340 is spherically shaped with a recess 346 shaped to receive a stabilizing rod 125 or 130 (130 not shown). The recess 346 is wider than the stabilizing rod 125 or 130 (130 not shown), and the bottom of the recess 346 includes two ramped portions 348a and 348b meeting at an apex 350. When the polyaxial link 340 is positioned on a stabilizing rod 125 or 130 (130 not shown), the stabilizing rod 125 or 130 (130 not shown) contacts at least the apex 350, which keeps the stabilizing rod 125 or 130 (130 not shown) centered in the recess 346, while the width of the recess 346 and the ramps 348a and 348b permit the polyaxial link 340 to be set at an angle to an axis of the stabilizing rod 125 or 130 (130 not shown) up a limit of, e.g., 10, 15, 20, 25, 30, 35, 40, 45, or more degrees, in any direction. When the stabilizing rod 125 or 130 (130 not shown) is at the desired angle in the recess 346 and the polyaxial link 340 is at the desired position on the stabilizing rod 125 or 130 (130 not shown), the adjustment nuts 344a and 344b can be used to lock the polyaxial link 340 in place. A locking pin 352 may also be used to further secure the stabilizing rod 125 or 130 (130 not shown) in place. The lower portion 354 of the polyaxial link 340 has a recess 356 shaped to receive a spinal rod 146, which is attached to the patient's spine (not shown). Each polyaxial link 340 can be positioned at a desired location on the spinal rod 146 and locked into place using, e.g, a set screw 358.

Figure 3E:
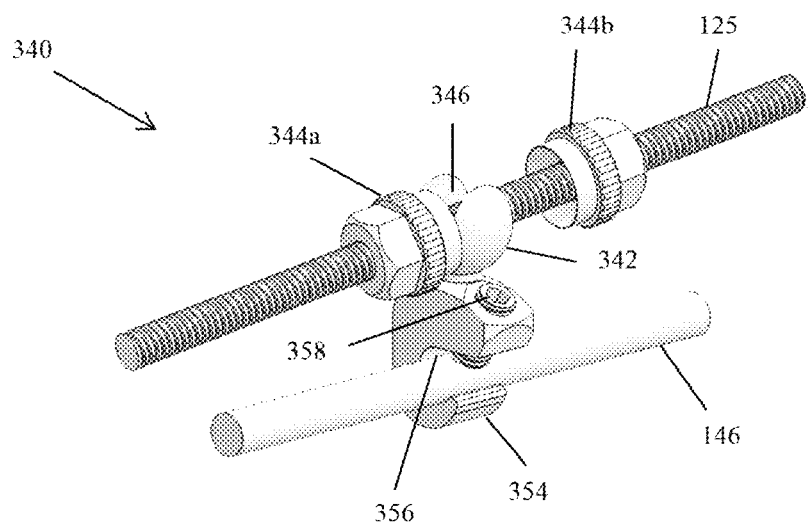
FIGS. 3E, 3F, 3G, and 3H show perspective views of the polyaxial link of FIG. 3D.
Figure 3F:
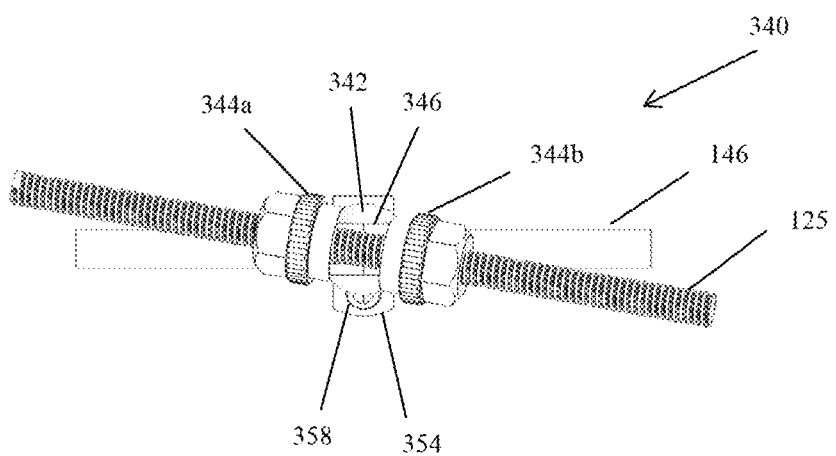
Figure 3G:
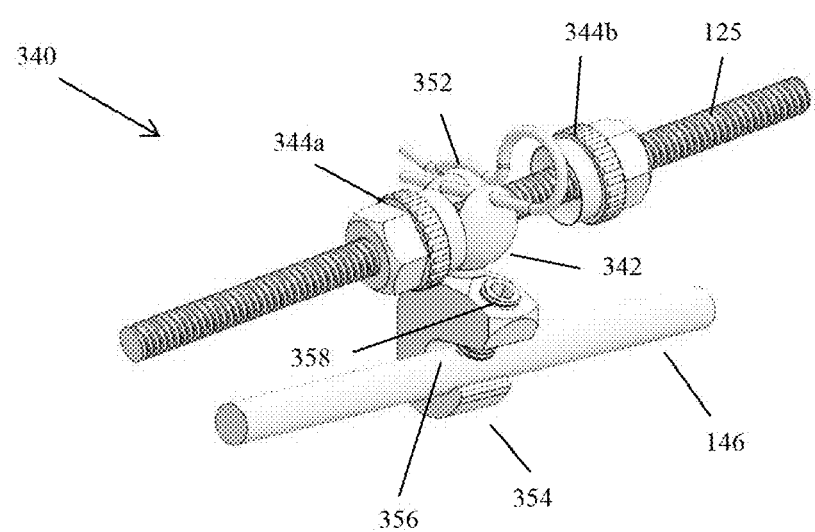
Figure 3H:
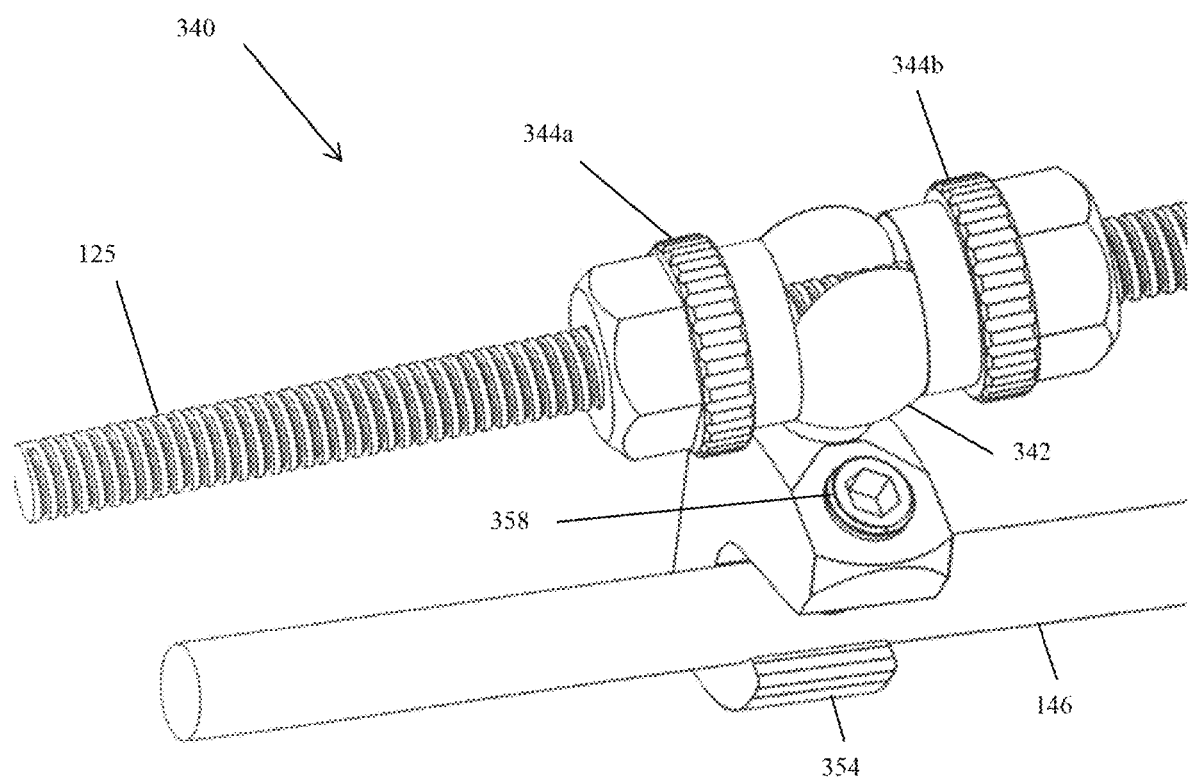

FIG. 3E illustrates the polyaxial link 340 with the adjustment nuts 344a, 344b disengaged. FIG. 3F shows the polyaxial link 340 from the top, with adjustment nuts 344a and 344b engaged, and locked into a position at an angle to the stabilizing rod 125. FIG. 3G illustrates the polyaxial link 340 with the adjustment nut 344a engaged and adjustment nut 344b disengaged and a locking pin 352 in place. FIG. 3H illustrates the polyaxial link 340 with the adjustment nuts 344a, 344b engaged.

Figure 3I:
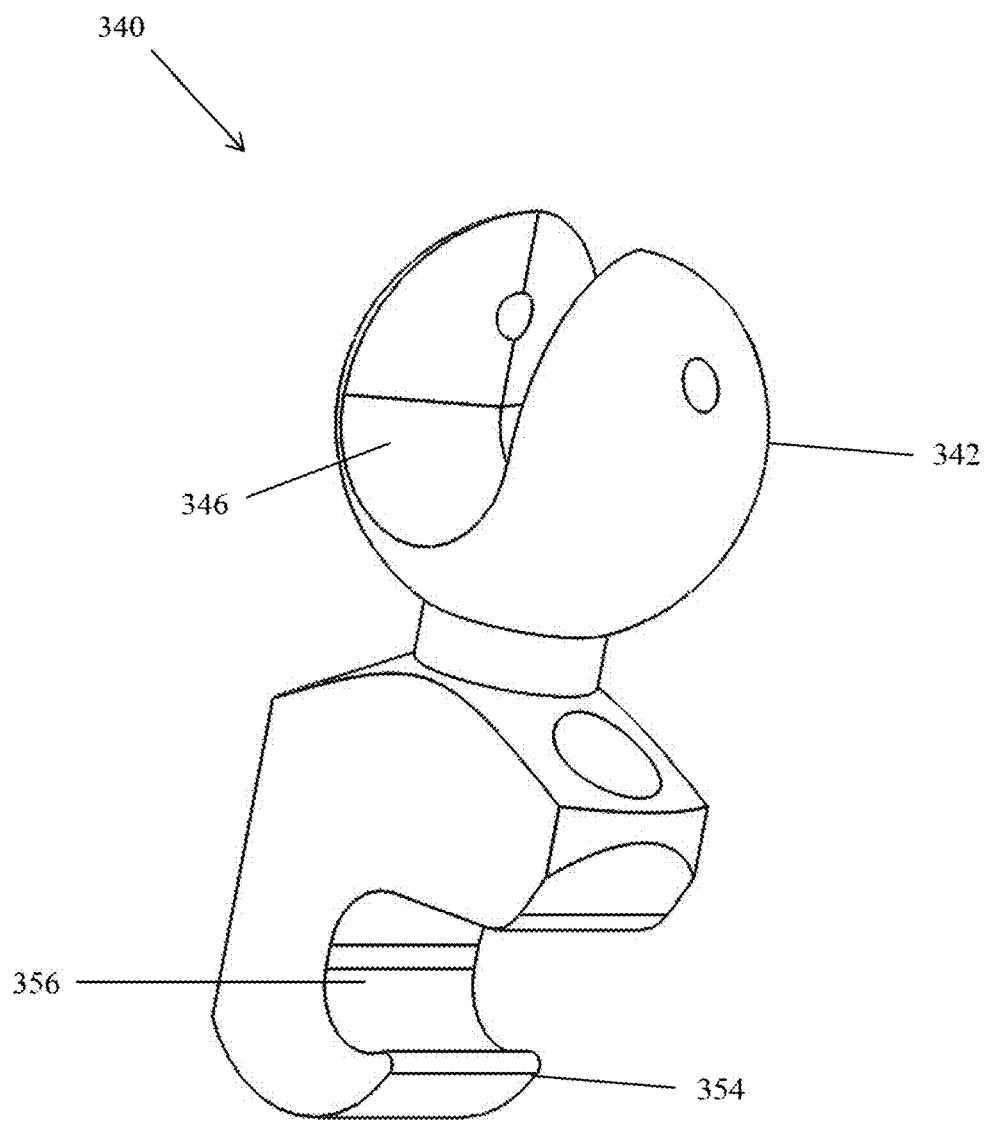
FIG. 3I shows a perspective view of another polyaxial link.

FIG. 3I shows a perspective view of the polyaxial link 340, showing the upper section 342, the recess 346, the lower portion 354, and the recess 356.

Figure 3J:
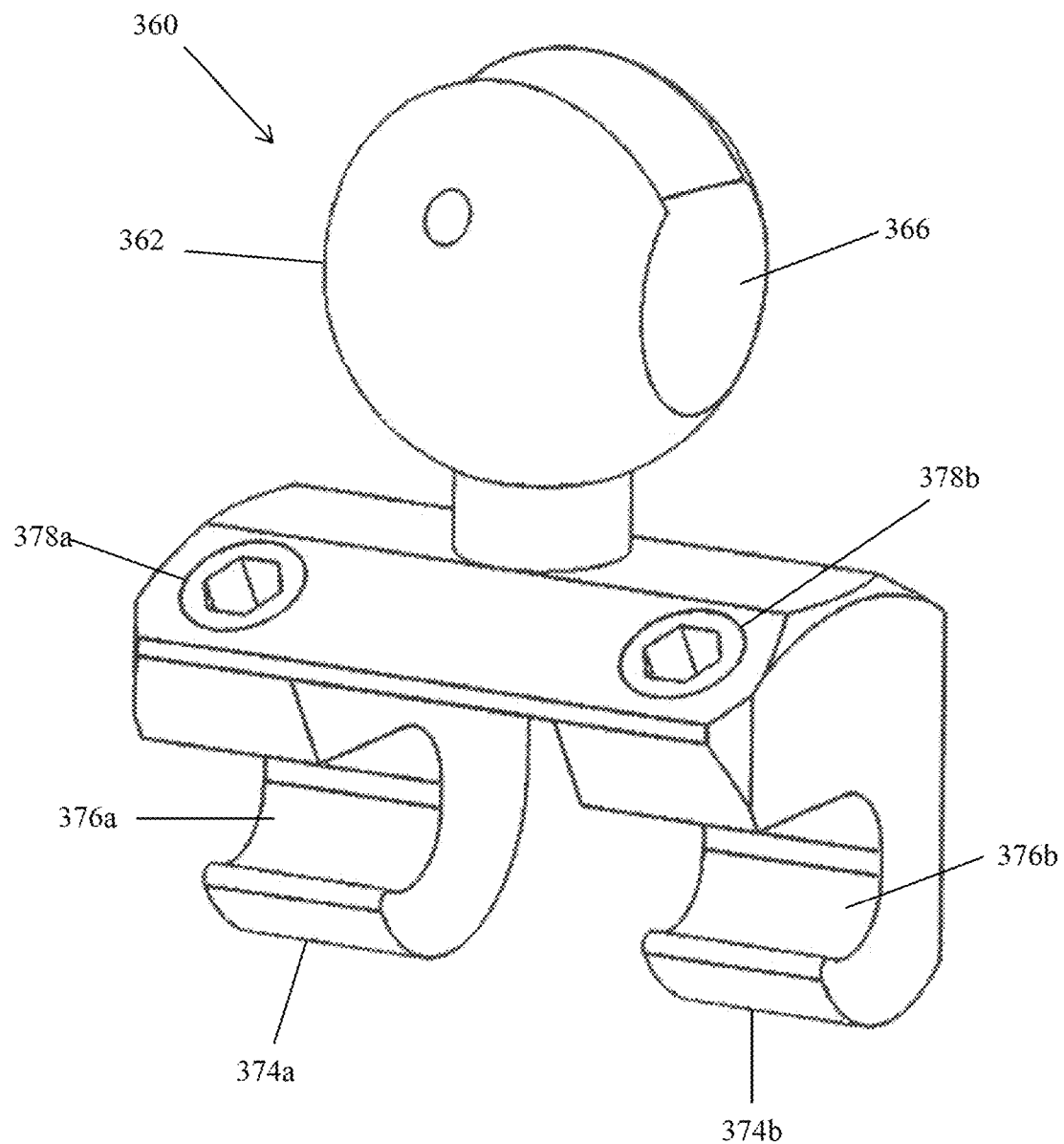
FIG. 3J shows a perspective view of still another polyaxial link.

FIG. 3J shows a perspective view of the polyaxial link 360. The polyaxial link 360 is similar to the polyaxial link 340 except that the bottom end 374 of the polyaxial link 360 has two components or prongs, 374a and 374b. The prongs 374a and 374b have recesses 376a and 376b, respectively, shaped to receive spinal rod 146 (not shown), permitting engagement with a spinal rod 146 at two places. The polyaxial link 360 can be locked into place on spinal rod 146 using screws 378a and 378b. Engagement of the polyaxial link 360 with spinal rod 146 at two places provides increased stability of the polyaxial link 360 when engaged, compared to single-component or -prong polyaxial links such as the polyaxial link 340. Among other features of the polyaxial link 360, FIG. 3J shows the upper portion 362 of the polyaxial link 360, with a recess 366 shaped to receive stabilizing rod 125 or 130 (neither are shown). The components or prong similar to prongs 374a and 374b may also be used on the monoaxial links disclosed herein.

Figure 4A:
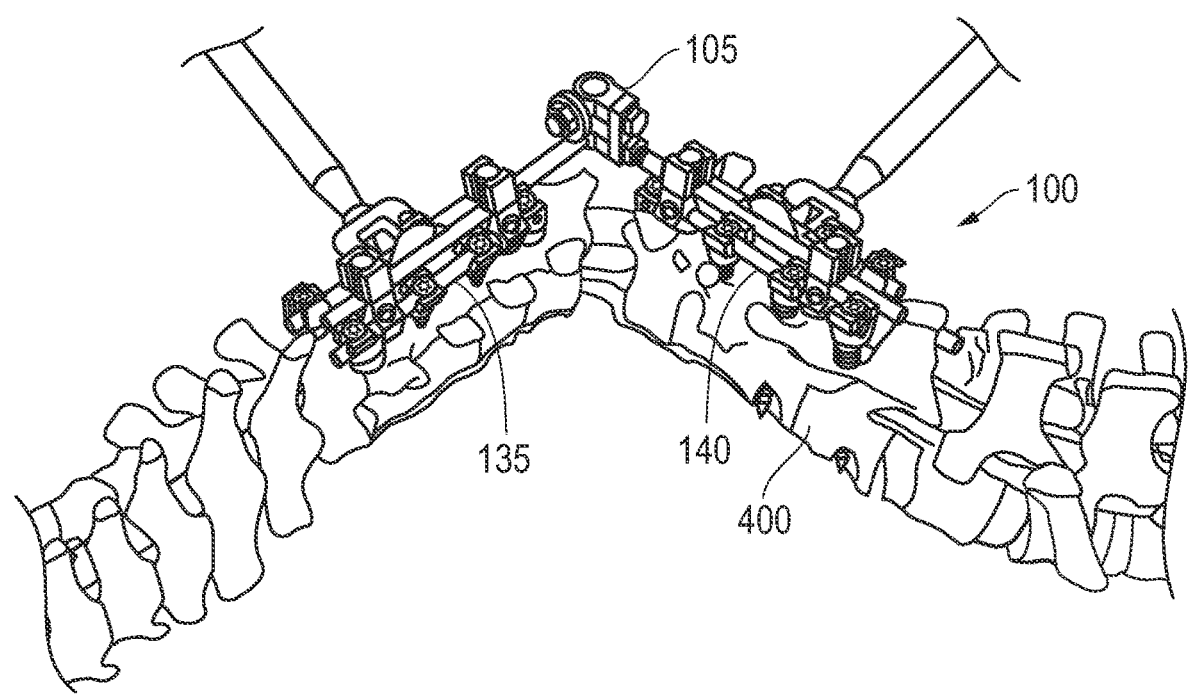
FIGS. 4A, 4B, and 4C illustrate the stabilizer assembly of FIGS. 1A, 1B, and 1C coupled to spinal rods, with the spinal rods attached to a simulated spine.
Figure 4B:
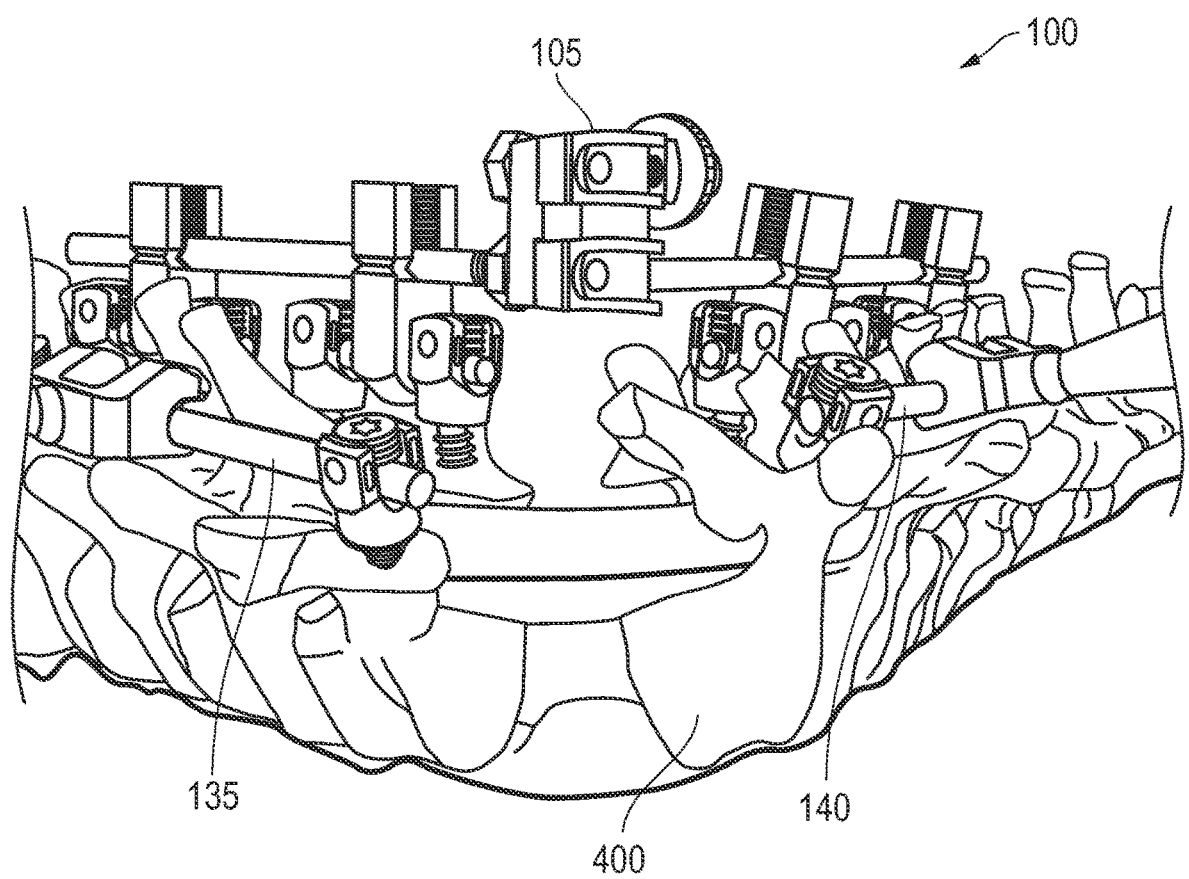
Figure 4C:
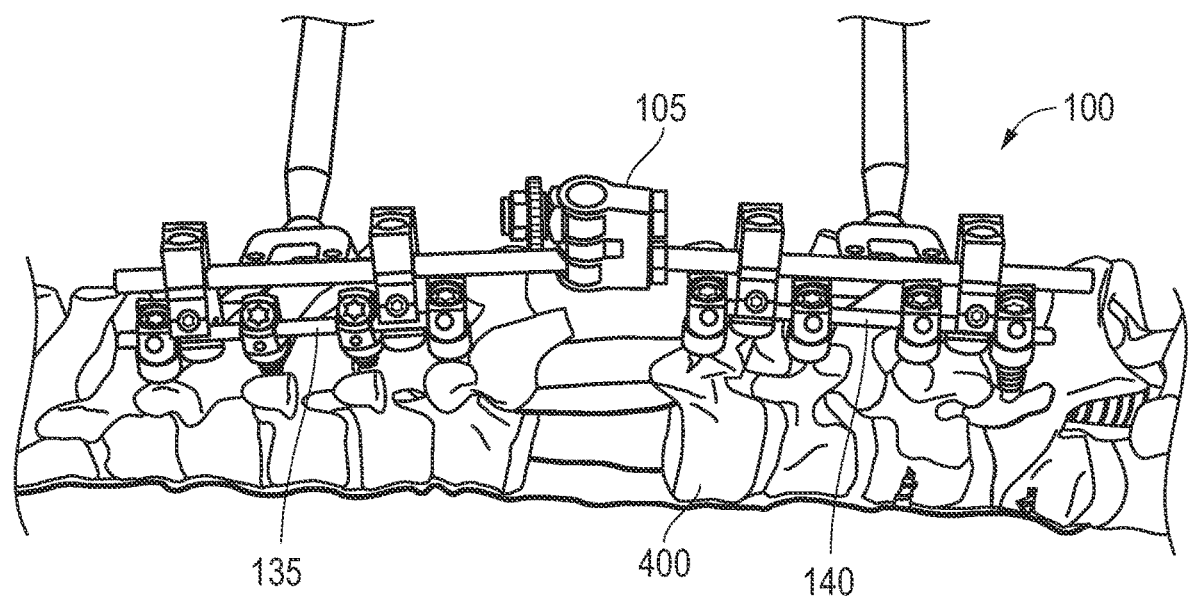

FIGS. 4A, 4B, and 4C illustrate the stabilizer assembly 100 of the present invention coupled to the spinal rods 135 and 140, with the spinal rods 135 and 140 attached to a simulated spine 400. FIGS. 4A and 4B illustrate the hinge 105 positioned at the apex of the spinal deformity, at which a VCR has been performed. FIG. 4C illustrate the hinge 105 positioned at the apex of the spinal deformity, at which the deformity has been corrected.

Figure 5A:
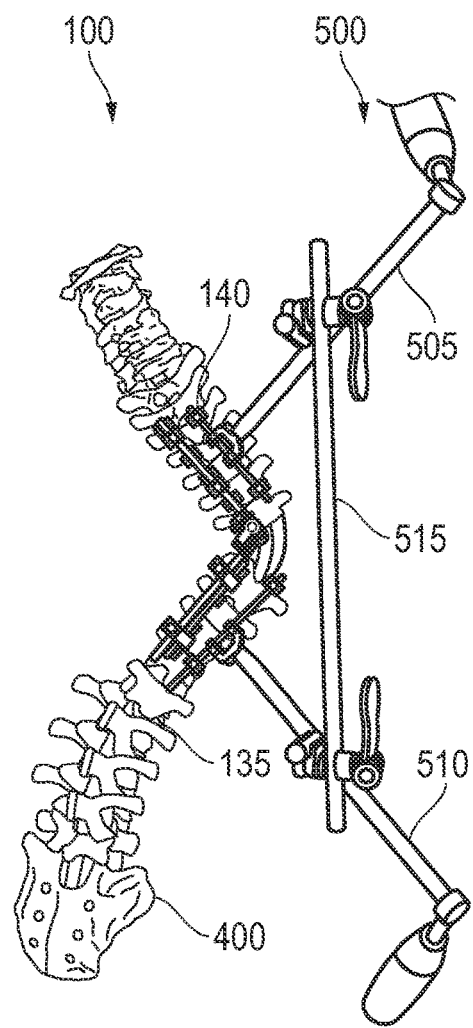
FIGS. 5A and 5B depicts the stabilizer assembly of FIGS. 1A, 1B, and 1C being used with a manipulator assembly.
Figure 5B:
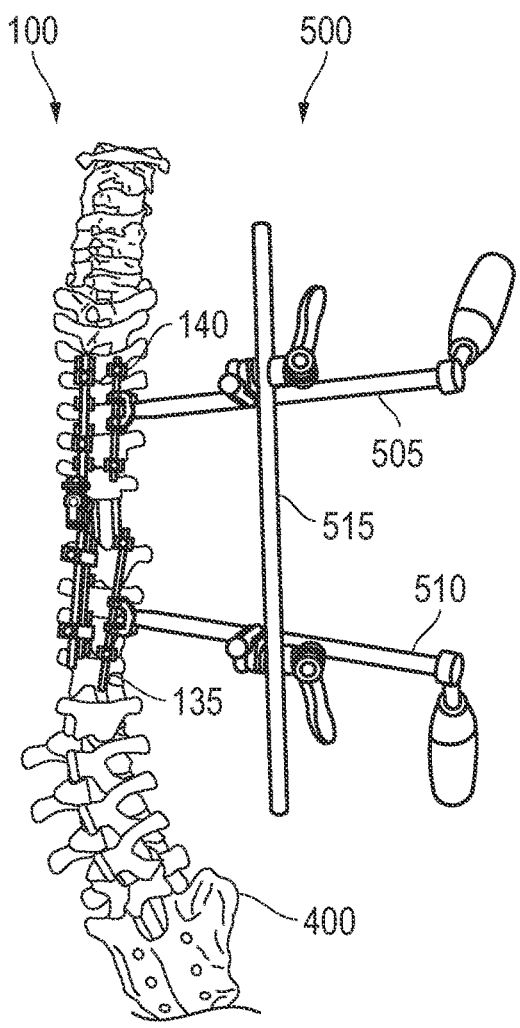

FIGS. 5A and 5B depict the stabilizer assembly 100 being used in conjunction with a manipulator assembly 500. FIGS. 5A and 5B illustrate how the stabilizer assembly 100 and the manipulator assembly 500 are used together to perform a spinal correction. Manipulator assembly 500 includes the handles 505 and 510 and the connecting rod 515. The connecting rod 515 is movably coupled by, e.g., one or more clamps or one or more screws, to the handles 505 and 510 to stabilize or fix the handles 505 and 510 relative to one another as desired. The handles 505 and 510 are couplable to spinal rods 135 and 140 to permit manipulation of the spine into a fixed configuration for the stabilizer assembly to maintain. FIGS. 5A and 5B show the manipulator assembly 500 coupled to two spinal rods 135 and 140, with the handles 505 and 510 in different relative positions and with the simulated spine 400 manipulated to two different desired configurations. The stabilizer assembly 100 is also shown.

Figure 6A:
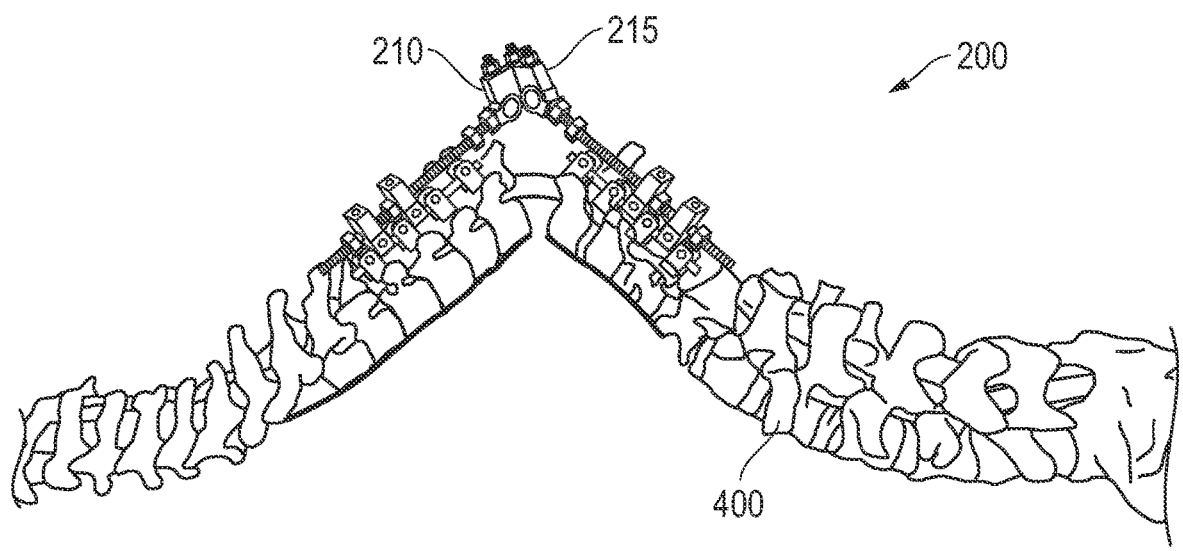
FIGS. 6A, 6B, and 6C show a coronal plane control correction, a sagittal plane control correction, and a longitudinal correction using the stabilizer assembly of FIG. 2A, respectively.
Figure 6B:
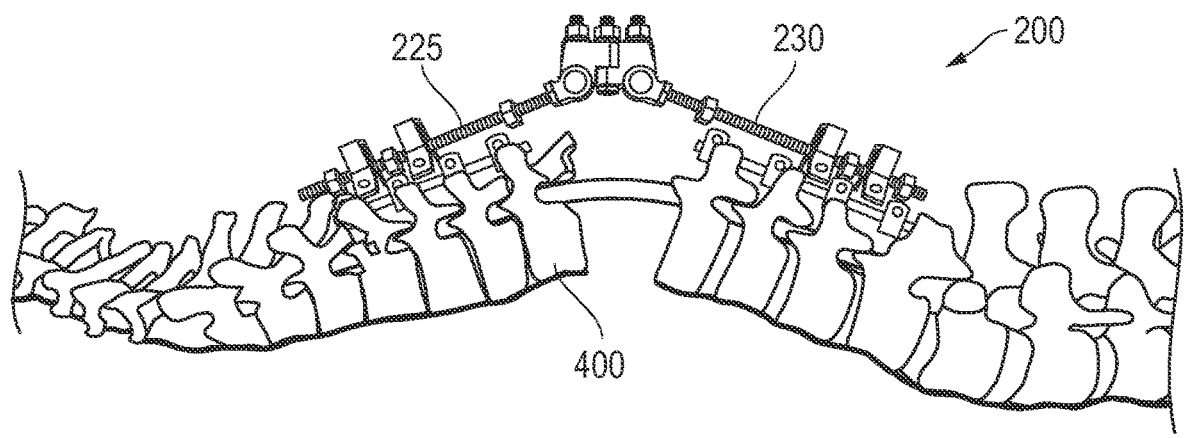
Figure 6C:
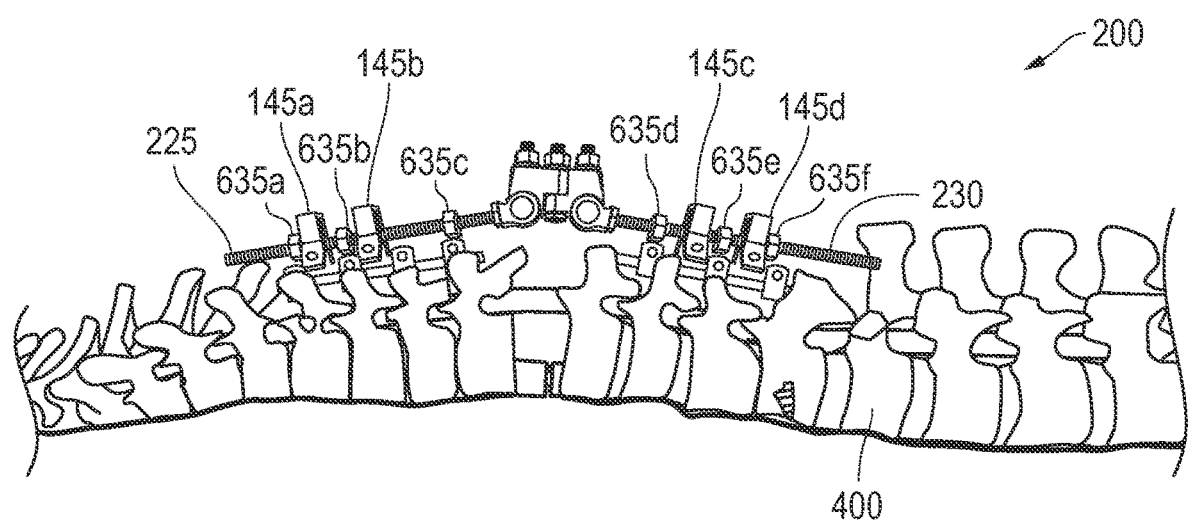

FIG. 6A depicts a coronal plane control correction using the stabilizer assembly 200. The rod-bearing leaves 210 and 215 are set at a desired angle to position the simulated spine 400 as desired. FIG. 6B depicts a sagittal plane control correction using the stabilizer assembly 200. The stabilizing rods 225 and 230 are set at desired positions to position the simulated spine 400 as desired. FIG. 6C depicts a longitudinal correction using the stabilizer assembly 200. The links 145a, 145b, 145c, and 145d are set at desired positions by the adjustment nuts 635a, 635b, 635c, 635d, 635e, and 635f.

Figure 6D:
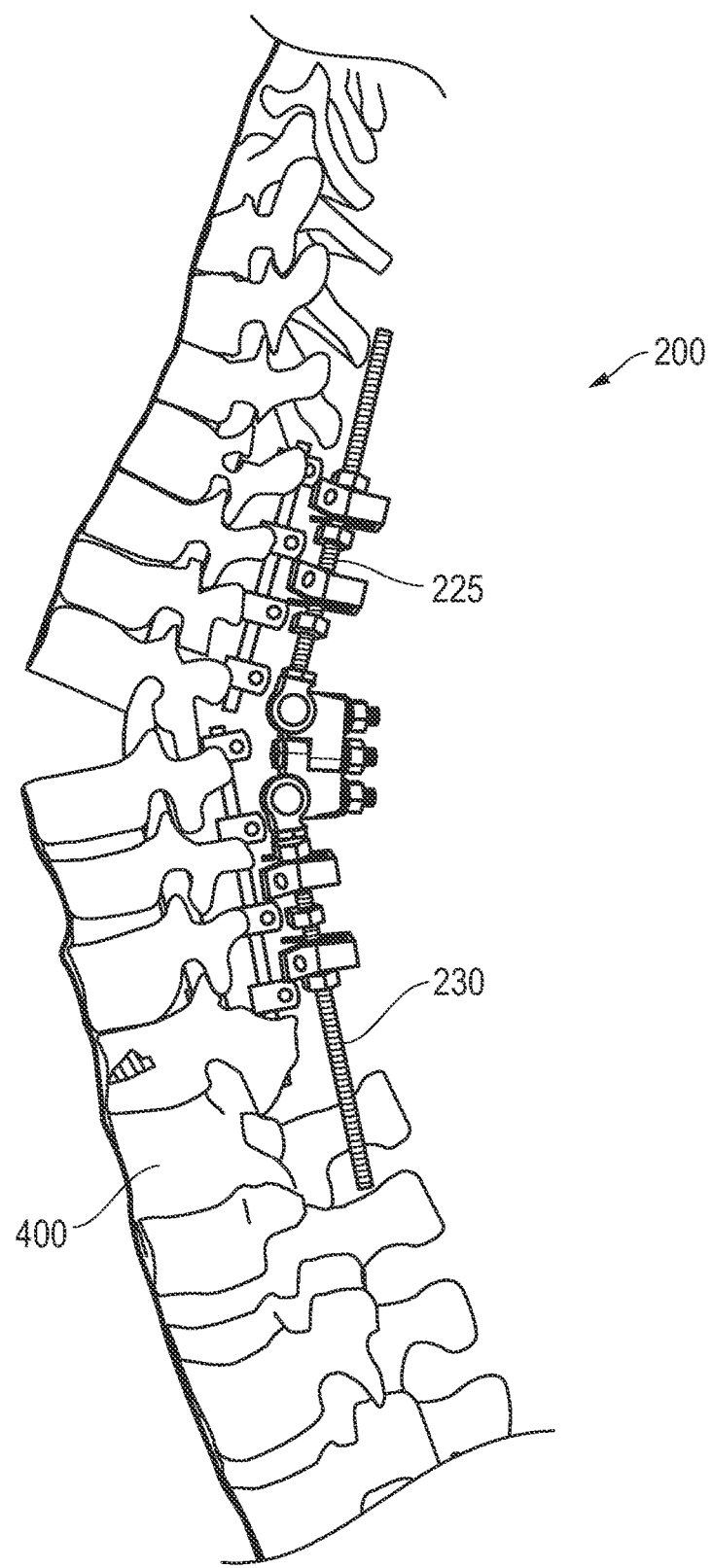
FIGS. 6D and 6E show two different sagittal plane control corrections using the stabilizer assembly of FIG. 2A.
Figure 6E:
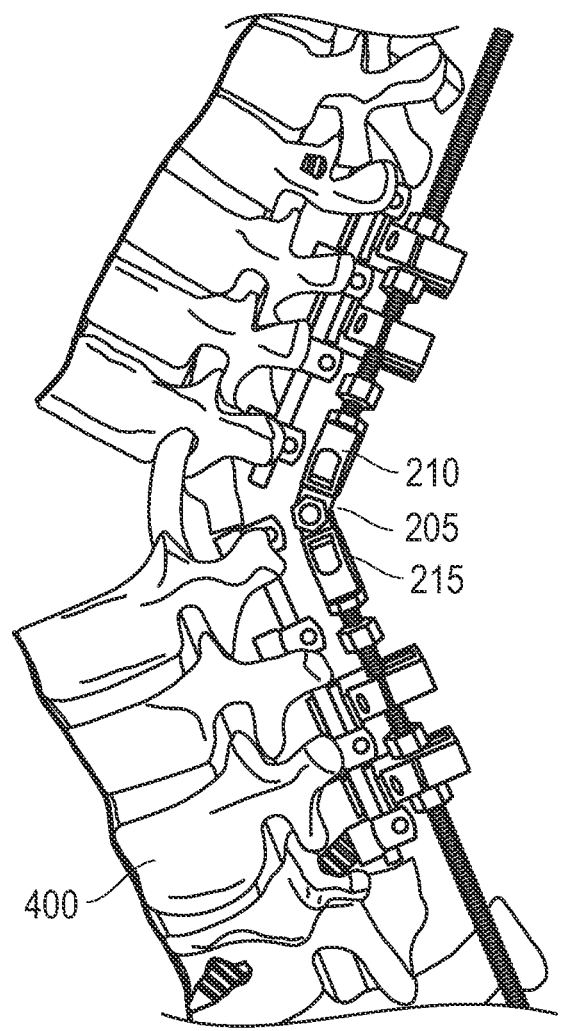
Figure 6F:
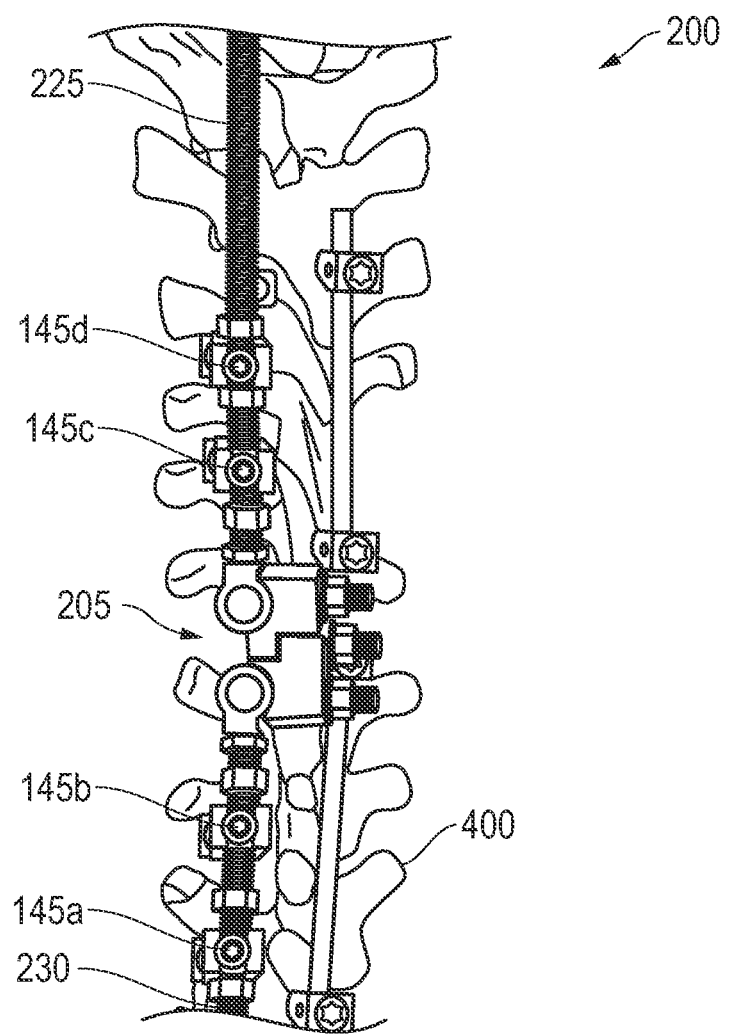
FIG. 6F illustrates a top view of the sagittal plane control correction of FIG. 6E.

FIG. 6D depicts a sagittal plane control correction using the stabilizer assembly 200. The stabilizing rods 225 and 230 are set at desired positions to position the simulated spine 400 as desired. FIG. 6E depicts a sagittal plane control correction using the stabilizer assembly 200. The stabilizer assembly 200 is rotated 90 degrees from the position shown in FIG. 6D to allow the hinge 205 to have sagittal freedom of motion. The rod-bearing leaves 210 and 215 of the hinge 205 are set at a desired angle to position the simulated spine 400 as desired. FIG. 6F depicts a top view of the sagittal plane control correction of FIG. 6E.

Figure 6G:
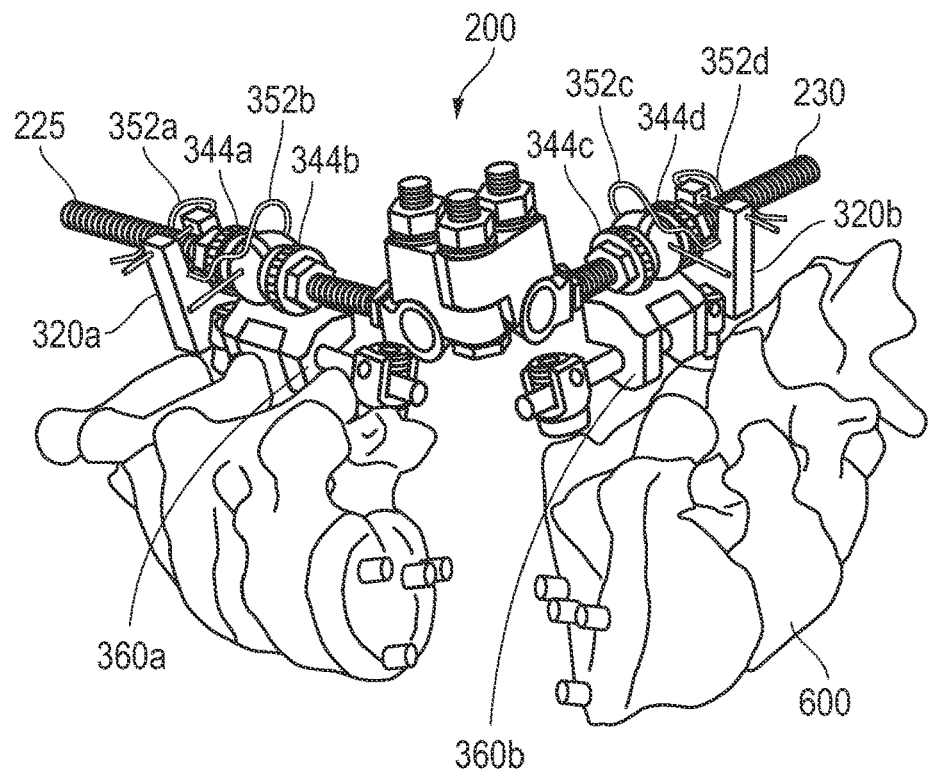
FIGS. 6G, 6H, 6I, and 6J show various views of stabilizer assembly of FIG. 2I.
Figure 6H:
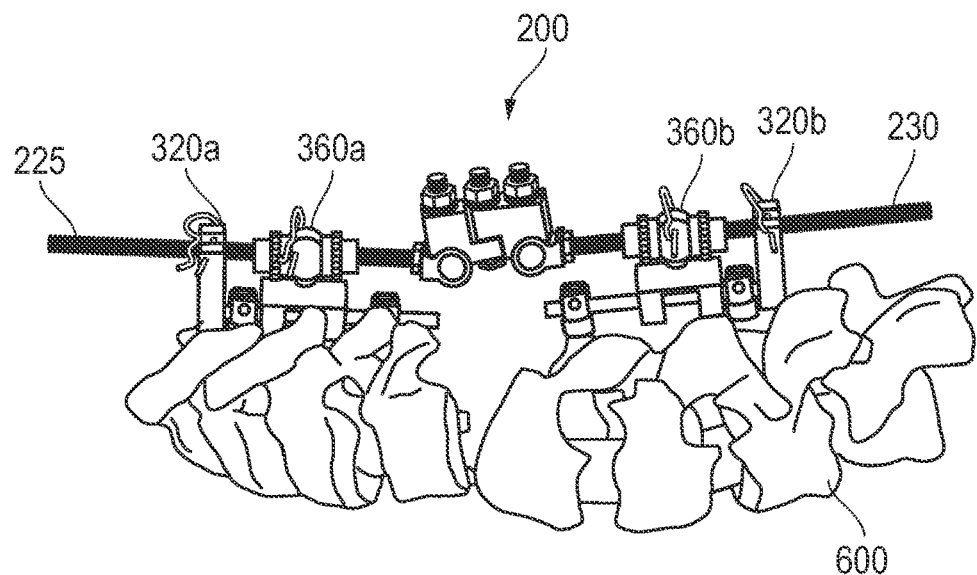
Figure 6I:
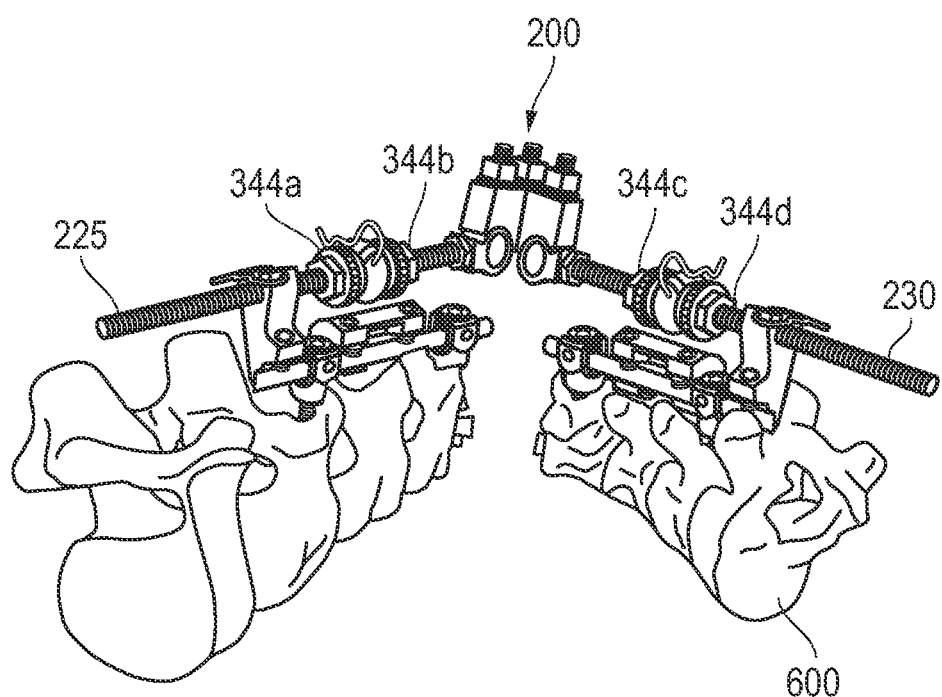
Figure 6J:
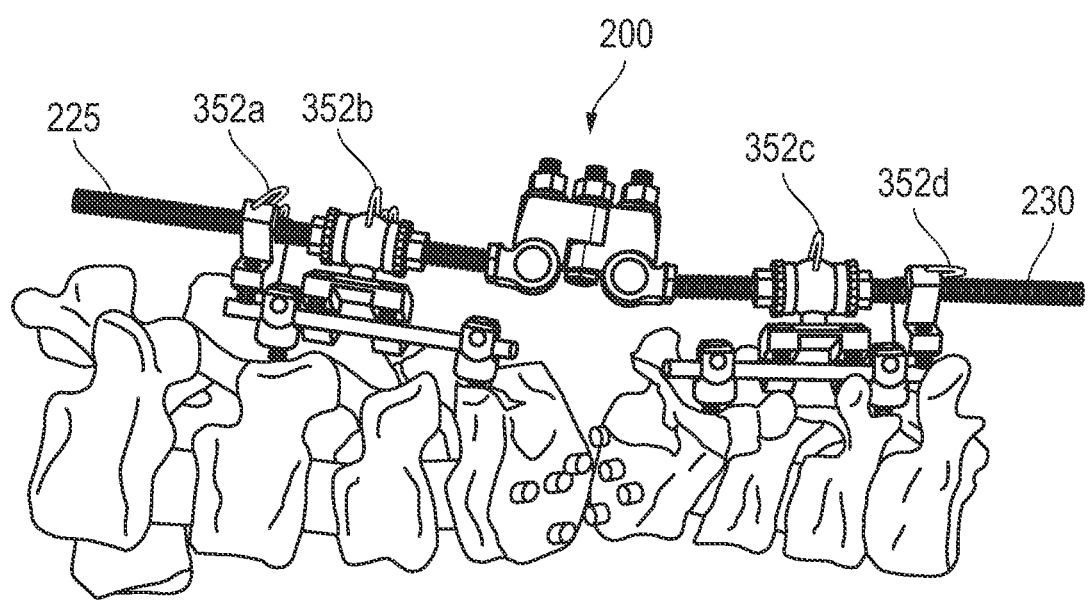

FIGS. 6G, 6H, 6I, and 6J show various views of stabilizer assembly 200 with adjustment nuts 344a, 344b, 344c, and 344d (where adjustment nuts 344c and 344d are similar to adjustment nuts 344a and 344b); retaining pins 352a, 352b, 352c, and 352d; polyaxial links 360a and 360b; and monoaxial links 320a and 320b mounted on stabilizing arms 225 and 230, with simulated spine 600. FIG. 6G indicates all of these items and illustrates the hinge 200 positioned at the apex of the spinal deformity, at which a VCR has been performed. FIG. 6H illustrates the hinge 200 positioned at the apex of the spinal deformity, at which the deformity has been corrected. FIG. 6I indicates another view (concave side view) of FIG. 6G. FIG. J indicates another view (concave side view) of FIG. 6H.

In FIGS. 6G, 6H, 6I, and 6J, adjustment nuts 344a, 344b, 344c, and 344d; polyaxial links 360a and 360b; and monoaxial links 320a and 320b include metal coated with Teflon®. All monoaxial links, polyaxial links, and adjustment nuts discussed herein may include metal, Teflon®, some combination, e.g., Teflon®-coated metal, polymers, composites, etc.

Figure 7A:
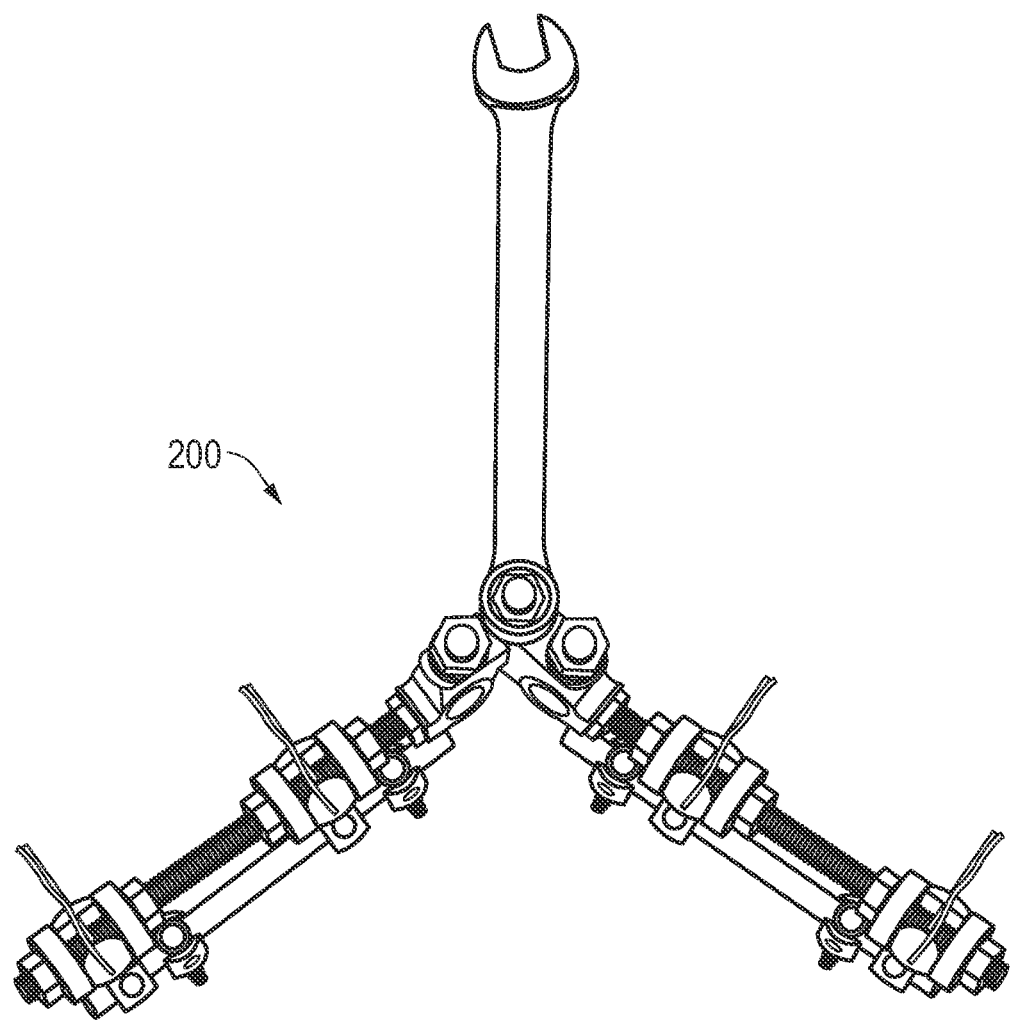
FIG. 7A shows a coronal plane control correction using the stabilizer assembly of FIG. 2I.
Figure 7B:
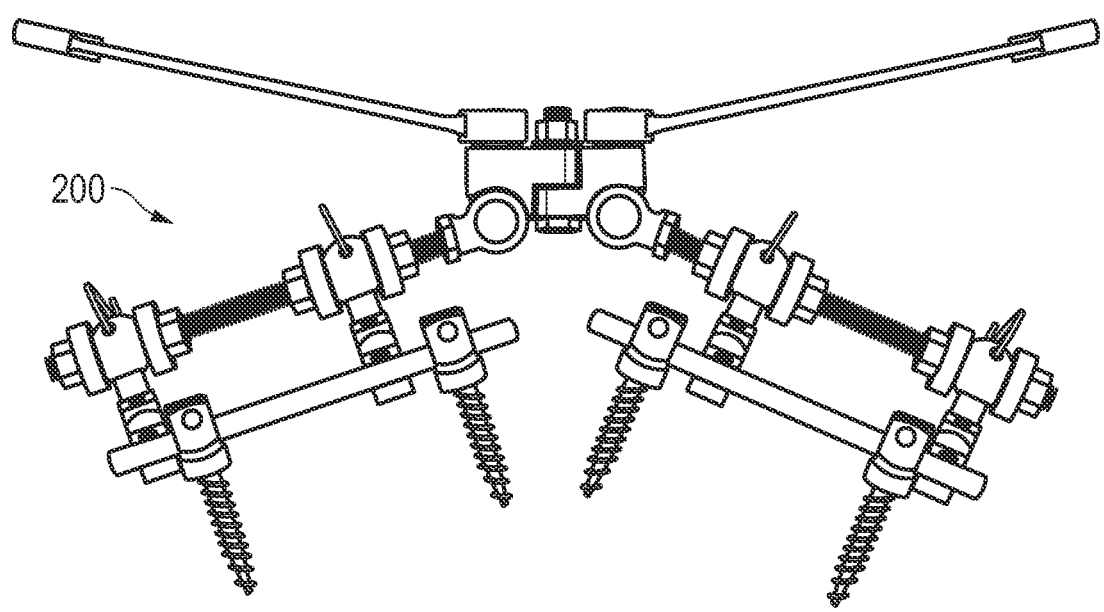
FIG. 7B shows a sagittal plane control correction using the stabilizer assembly of FIG. 2I.
Figure 7C:
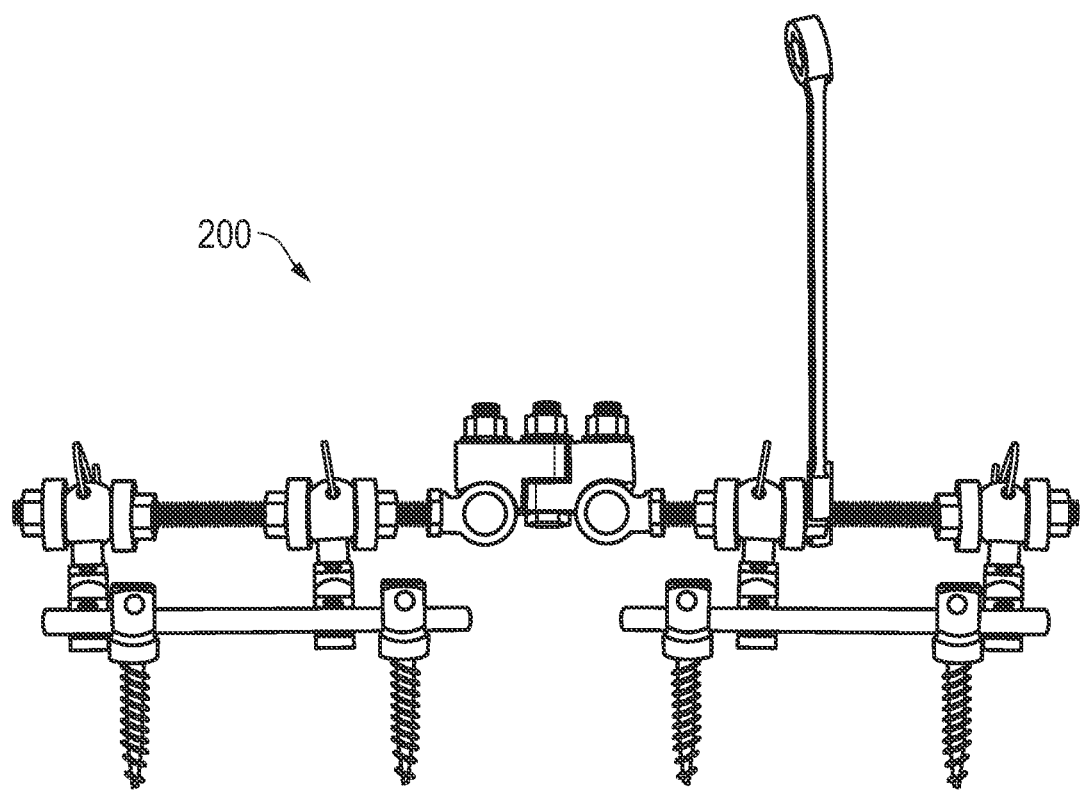
FIG. 7C shows a longitudinal correction using the stabilizer assembly of FIG. 2I.
Figure 7D:
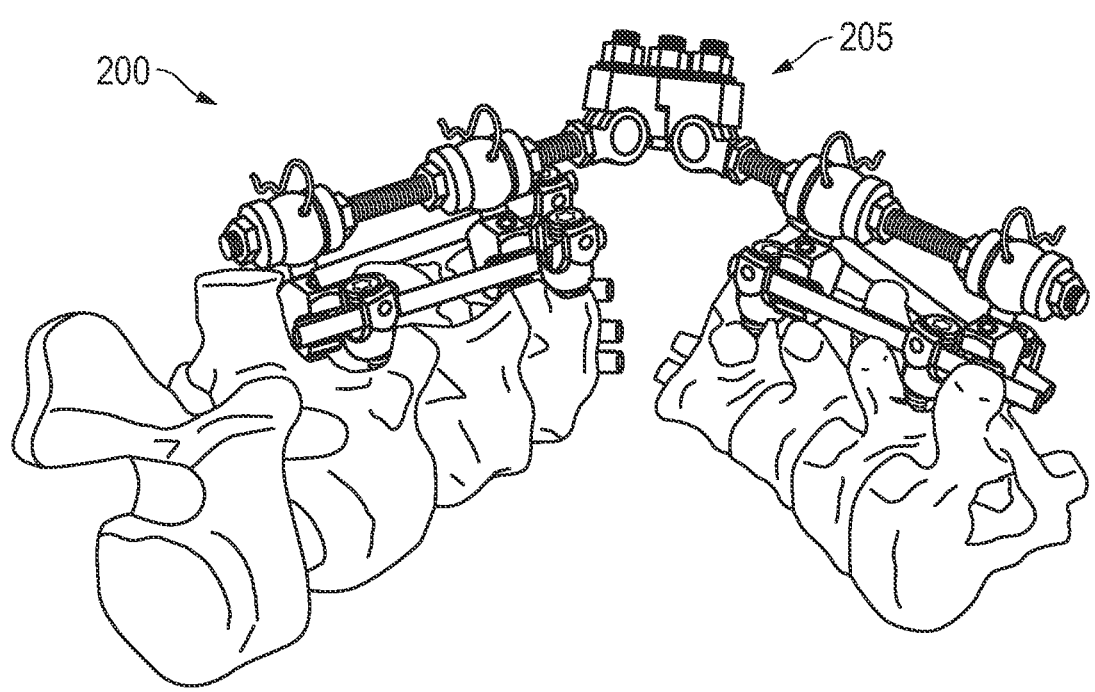
FIG. 7D shows the stabilizer assembly of FIG. 2I with the hinge positioned at the apex of a spinal deformity, at which a VCR has been performed.
Figure 7E:
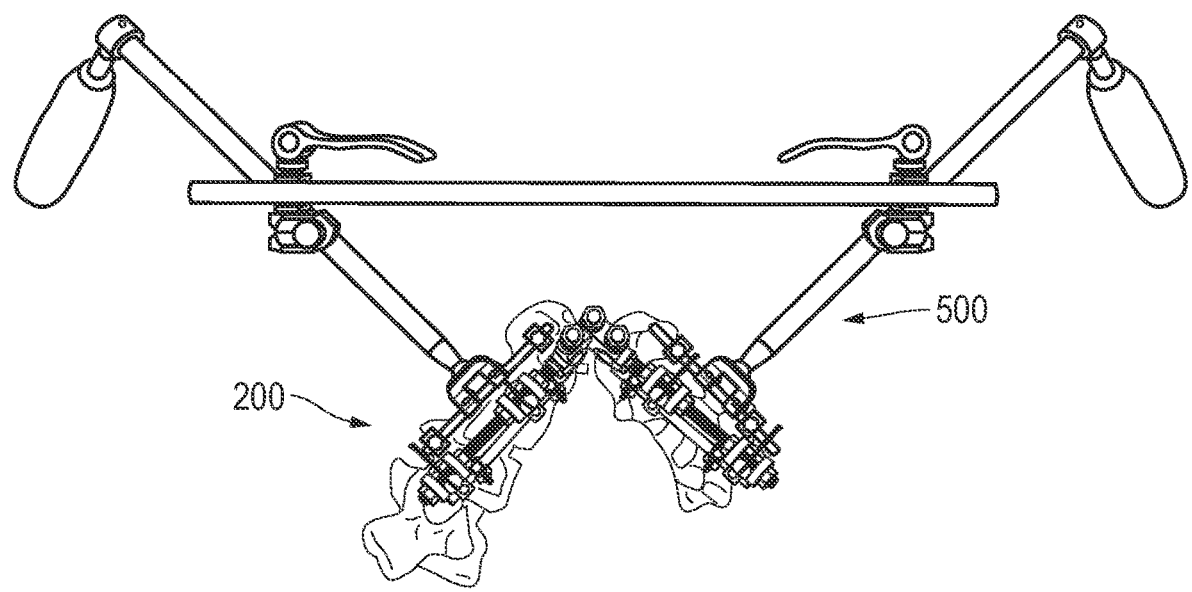
FIGS. 7E and 7F show how the hinge of the stabilizer assembly of FIG. 2I and the manipulator assembly of FIGS. 5A and 5B are used together to perform a spinal correction.
Figure 7F:
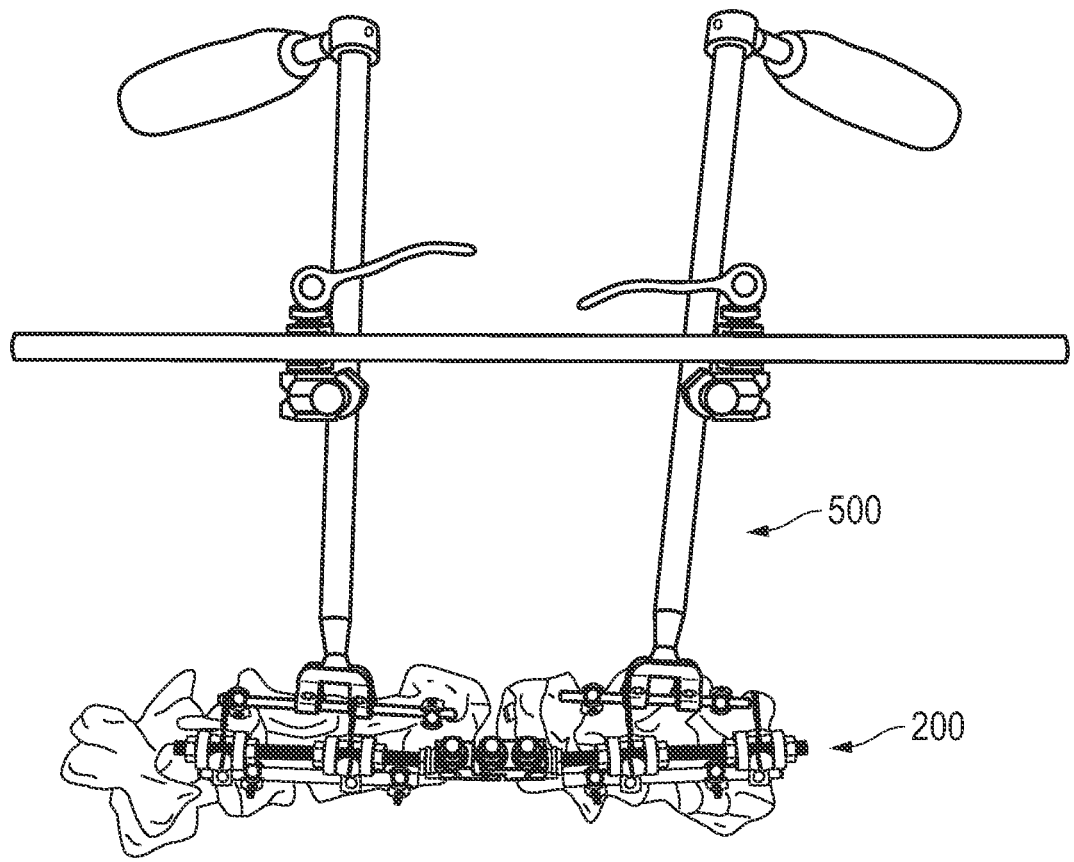
Figure 7G:
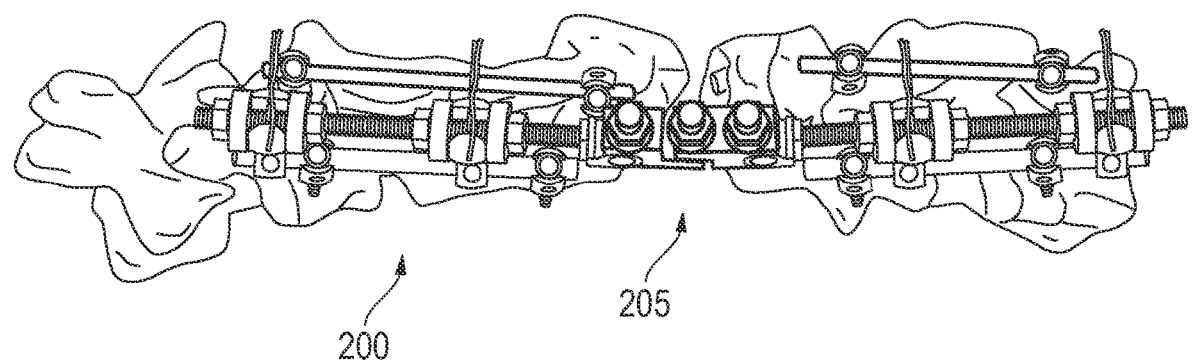
FIG. 7G shows how the hinge of the stabilizer assembly of FIG. 2I is used to stabilize the spinal correction of FIGS. 7E and 7F.

FIGS. 7A-7G illustrate various uses of the stabilizer assembly 200 of FIG. 2I. FIG. 7A shows a coronal plane control correction using the stabilizer assembly 200. FIG. 7B shows a sagittal plane control correction using the stabilizer assembly 200. FIG. 7C depicts a longitudinal correction using the stabilizer assembly 200. FIG. 7D shows the stabilizer assembly 200 with the hinge 205 positioned at the apex of a spinal deformity, at which a VCR has been performed. FIGS. 7E and 7F illustrate how the hinge of the stabilizer assembly 200 and the manipulator assembly 500 of FIGS. 5A and 5B are used together to perform a spinal correction. FIG. 7G depicts how the hinge 205 of the stabilizer assembly 200 is used to stabilize the spinal correction of FIGS. 7E and 7F.

Embodiments of the present invention can be used in conjunction with existing instruments, tools, and other devices generally used in treating spinal conditions.

Components of the present invention, including the stabilizer assembly and the polyaxial links, may be made of a non-organic material that is durable and that can be implanted in a human body, such as titanium, stainless steel, spring steel, aluminum, niobium, carbon fiber, ceramics, polymers, composites or any relatively hard material (e.g. Titanium-Aluminium-Niobium-alloy). Generally, the material selected will be biocompatible, that is, compatible with the surrounding bone and tissue.

Figure 8:
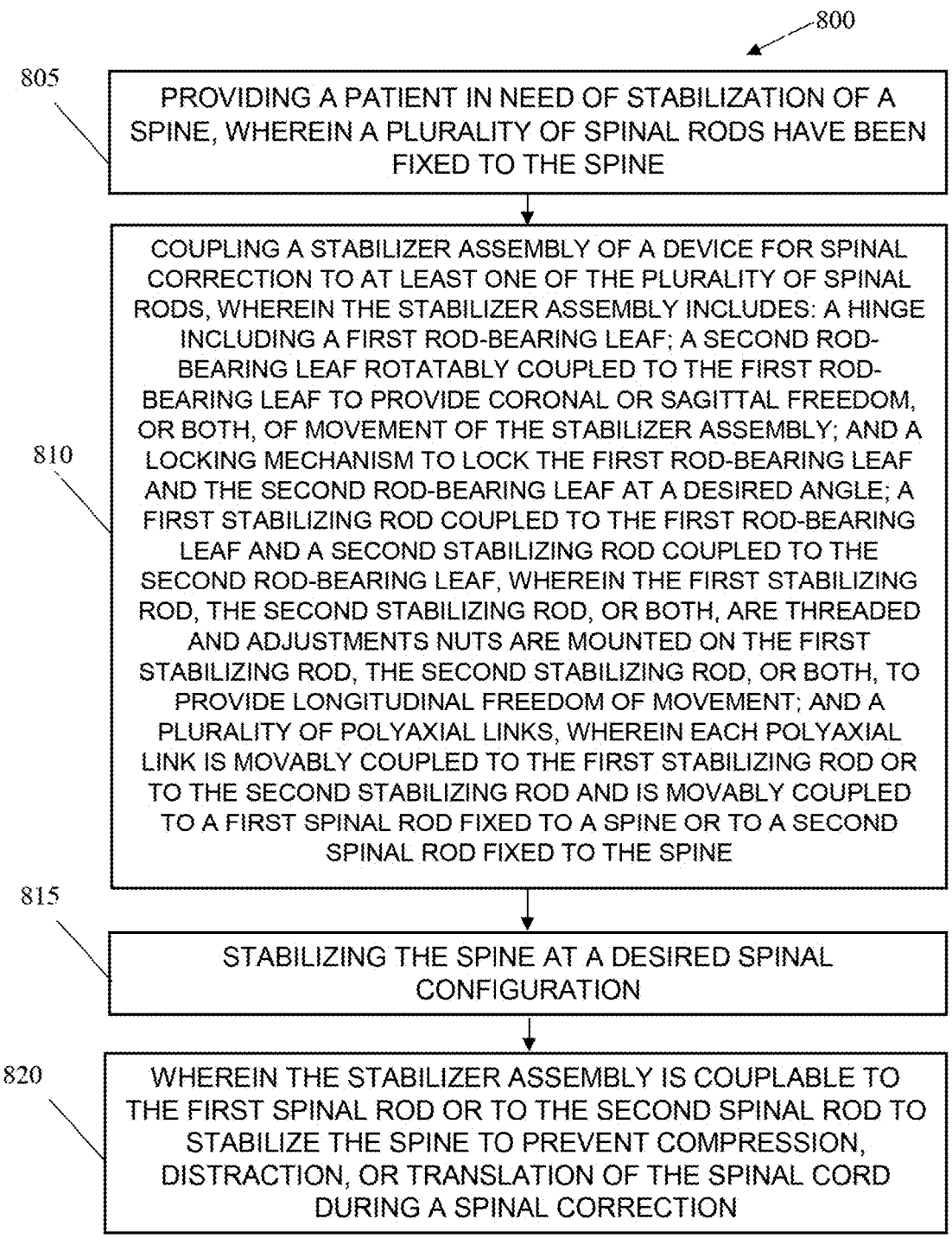
FIG. 8 depicts a flowchart of a method embodiment of the present invention.

FIG. 8 depicts a flowchart of a method embodiment of the present invention. Method 800 of stabilizing a spine includes block 805, providing a patient in need of stabilization of a spine, wherein a plurality of spinal rods have been fixed to the spine. Block 810 includes coupling a stabilizer assembly of a device for spinal correction to at least one of the plurality of spinal rods, wherein the stabilizer assembly includes a hinge including a first rod-bearing leaf; a second rod-bearing leaf rotatably coupled to the first rod-bearing leaf to provide coronal or sagittal freedom of movement, or both, of the stabilizer assembly; and a locking mechanism to lock the first rod-bearing leaf and the second rod-bearing leaf at a desired angle; a first stabilizing rod coupled to the first rod-bearing leaf and a second stabilizing rod coupled to the second rod-bearing leaf, wherein the first stabilizing rod, the second stabilizing rod, or both, are threaded and adjustment nuts are mounted on the first stabilizing rod, the second stabilizing rod, or both, to provide longitudinal freedom of movement; and a plurality of polyaxial links, wherein each polyaxial link is movably coupled to the first stabilizing rod or to the second stabilizing rod and is movably coupled to a first spinal rod fixed to a spine or to a second spinal rod fixed to the spine. Included in block 815 is fixing the spine at a desired spinal configuration. In block 820, the stabilizer assembly is couplable to the first spinal rod or to the second spinal rod to stabilize the spine to prevent compression, distraction, or translation of the spinal cord during a spinal correction.

One skilled in the art of medical treatment of human hip ailments will recognize that the device for treating spinal maladies including stabilizer assembly 100, stabilizer assembly 200, and method 700 provide effective methods and systems that reduce risk for compression, distraction, or translation of the spinal cord during stabilization, manipulation, and fixation of a deformed spine subject to a vertebral column resection surgery or a spinal correction.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of." As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step, or a limitation) or group of integers (e.g., feature(s), element(s), characteristic(s), property(ies), method/process(s) steps, or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about," "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the devices and/or methods disclosed and claimed herein can be made and executed without undue experimentation in light of the present disclosure. While the devices and/or methods of this invention have been described in terms of particular embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope, and concept of the invention as defined by the appended claims.

Furthermore, no limitations are intended to the details of construction or design herein shown, other than as described in the claims below. It is therefore evident that the particular embodiments disclosed above may be altered or modified and all such variations are considered within the scope and spirit of the disclosure. Accordingly, the protection sought herein is as set forth in the claims below.

Modifications, additions, or omissions may be made to the systems and apparatuses described herein without departing from the scope of the invention. The components of the systems and apparatuses may be integrated or separated. Moreover, the operations of the systems and apparatuses may be performed by more, fewer, or other components. The methods may include more, fewer, or other steps. Additionally, steps may be performed in any suitable order.

To aid the Patent Office, and any readers of any patent issued on this application in interpreting the claims appended hereto, applicants wish to note that they do not intend any of the appended claims to invoke 35 U.S.C. § 112(f) as it exists on the date of filing hereof unless the words "means for" or "step for" are explicitly used in the particular claim.

What is claimed is:

1. A device for spinal correction comprising:
   a stabilizer assembly comprising:
   a hinge comprising:
      a first rod-bearing leaf;
      a second rod-bearing leaf rotatably coupled to the first rod-bearing leaf to provide coronal or sagittal freedom of movement, or both, of the stabilizer assembly;
      a locking mechanism to lock the first rod-bearing leaf and the second rod-bearing leaf at a desired angle;
   a first stabilizing rod coupled to the first rod-bearing leaf;
   a second stabilizing rod coupled to the second rod-bearing leaf; and
   a plurality of polyaxial links;
   wherein each polyaxial link comprises a spherical upper end with an upper linear slot within the spherical upper end, the upper linear slot configured to receive either the first stabilizing rod or the second stabilizing rod longitudinally, the upper linear slot being wider than the first or second stabilizing rod and comprising two flat ramped upper linear slot portions within the upper linear slot that meet at an apex within the upper linear slot and between the two flat ramped upper linear slot portions; and a lower end integral with or physically connected to the spherical upper end, the lower end having one or more lower recesses configured to receive a first spinal rod fixed to a spine or a second spinal rod fixed to the spine, wherein the polyaxial link is operable to position the first stabilizing rod or the second stabilizing rod at a range of angles to the first spinal rod or the second spinal rod;

wherein each polyaxial link is movably couplable to the first stabilizing rod or to the second stabilizing rod and is movably couplable to the first spinal rod fixed to the spine and to the second spinal rod fixed to the spine; and wherein the stabilizer assembly is couplable to the first spinal rod and to the second spinal rod to stabilize the spine to prevent compression, distraction, or translation of the spinal cord during a spinal correction.

2. The device of claim 1, wherein the locking mechanism to lock the first rod-bearing leaf and the second rod-bearing leaf at the desired angle comprises one or more screws.

3. The device of claim 1, wherein the first stabilizing rod is coupled to the first rod-bearing leaf with a first threaded portion of the first stabilizing rod.

4. The device of claim 1, wherein the second stabilizing rod is coupled to the second rod-bearing leaf with a second threaded portion of the second stabilizing rod.

5. The device of claim 1, wherein each polyaxial link is movably coupled to the first stabilizing rod or to the second stabilizing rod with one or more adjustment nuts or one or more locking pins.

6. The device of claim 1, wherein each polyaxial link is movable to and lockable at a position on the first stabilizing rod or the second stabilizing rod and is movable to and lockable at an angle to the first stabilizing rod or the second stabilizing rod with two or more adjustment nuts.

7. The device of claim 1, wherein each polyaxial link is movably couplable to the first spinal rod or to the second spinal rod at one or more components, each comprising a recess shaped to receive the first spinal rod or to the second spinal rod, and lockable in position with one or more screws.

8. The device of claim 1, wherein the first stabilizing rod is rotatably coupled to the first rod-bearing leaf to provide coronal or sagittal freedom of movement, or both, of the first stabilizing rod or the second stabilizing rod is rotatably coupled to the second rod-bearing leaf to provide coronal or sagittal freedom of movement, or both, of the second stabilizing rod;

and wherein the first stabilizing rod has a locking mechanism to lock it at a desired position or the second stabilizing rod has a locking mechanism to lock it at a desired position.

9. The device of claim 1, wherein the first stabilizing rod or the second stabilizing rod is threaded and adjustment nuts are mounted on the first stabilizing rod or the second stabilizing rod to provide longitudinal freedom of movement or locking of one or more of the plurality of polyaxial links on the first stabilizing rod or the second stabilizing rod.

10. A kit for a device for spinal correction comprising:
the device for spinal correction comprising:
a stabilizer assembly comprising:
a hinge comprising:
a first rod-bearing leaf;
a second rod-bearing leaf rotatably coupled to the first rod-bearing leaf to provide coronal or sagittal freedom of movement, or both, of the stabilizer assembly;
a locking mechanism to lock the first rod-bearing leaf and the second rod-bearing leaf at a desired angle;
a first stabilizing rod coupled to the first rod-bearing leaf;
a second stabilizing rod coupled to the second rod-bearing leaf; and
a plurality of links comprising a plurality of one or more monoaxial links and one or more polyaxial links;
wherein each monoaxial link comprises an upper end with an upper recess configured to receive the first or second stabilizing rod; a lower end with one or more lower recesses configured to receive a first spinal rod fixed to a spine or a second spinal rod fixed to the spine;
wherein each polyaxial link comprises a spherical upper end with an upper linear slot within the spherical upper end, the upper linear slot configured to receive either the first stabilizing rod or the second stabilizing rod longitudinally, the upper linear slot being wider than the first or second stabilizing rod and comprising two flat ramped upper recess portions within the upper linear slot that meet at an apex within the upper linear slot and between the two flat ramped upper linear slot portions; and a lower end integral with or physically connected to the spherical upper end, the lower end having one or more lower recesses configured to receive the first spinal rod or the second spinal rod, wherein the polyaxial link is operable to position the first stabilizing rod or the second stabilizing rod at a range of angles to the first spinal rod or the second spinal rod;
wherein each monoaxial and polyaxial link is movably couplable to the first stabilizing rod or to the second stabilizing rod and is movably couplable to a first spinal rod fixed to a spine and to a second spinal rod fixed to the spine; and
wherein the stabilizer assembly is couplable to the first spinal rod and to the second spinal rod to stabilize the spine to prevent compression, distraction, or translation of the spinal cord during a spinal correction;
one or more screws, one or more adjustment nuts, or one or more locking pins for use with the device for spinal correction; and
one or more tools for manipulation of the first and second stabilizing rods, the one or more screws, the one or more adjustment nuts, or the one or more locking pins.

11. The kit of claim 10, wherein the first stabilizing rod is rotatably coupled to the first rod-bearing leaf to provide coronal or sagittal freedom of movement, or both, of the first stabilizing rod or the second stabilizing rod is rotatably coupled to the second rod-bearing leaf to provide coronal or sagittal freedom of movement, or both, of the second stabilizing rod;

and wherein the first stabilizing rod has a locking mechanism to lock it at a desired position or the second stabilizing rod has a locking mechanism to lock it at a desired position.

12. The kit of claim 10, wherein the first stabilizing rod or the second stabilizing rod is threaded and adjustment nuts are mounted on the first stabilizing rod or the second stabilizing rod to provide longitudinal freedom of movement or locking of one or more of the plurality of one or more monoaxial links and one or more polyaxial links on the first stabilizing rod or the second stabilizing rod.

13. A method of stabilizing a spine comprising:
providing a patient in need of stabilization of a spine, wherein a plurality of spinal rods have been fixed to the spine;
coupling a stabilizer assembly of a device for spinal correction to at least one of the plurality of spinal rods, wherein the stabilizer assembly comprises:
a hinge comprising:
a first rod-bearing leaf;
a second rod-bearing leaf rotatably coupled to the first rod-bearing leaf to provide coronal or sagittal freedom of movement, or both, of the stabilizer assembly; and
a locking mechanism to lock the first rod-bearing leaf and the second rod-bearing leaf at a desired angle;
a first stabilizing rod coupled to the first rod-bearing leaf;
a second stabilizing rod coupled to the second rod-bearing leaf; and
a plurality of links comprising (1) a plurality of monoaxial links, (2) a plurality of polyaxial links, or (3) a plurality of one or more monoaxial links and one or more polyaxial links;
wherein each monoaxial link comprises an upper end with an upper recess configured to receive the first or second stabilizing rod; a lower end with one or more lower recesses configured to receive a first spinal rod fixed to a spine or a second spinal rod fixed to the spine;
wherein each polyaxial link comprises a spherical upper end with an upper linear slot within the spherical upper end, the upper linear slot configured to receive either the first stabilizing rod or the second stabilizing rod longitudinally, the upper linear slot being wider than the first or second stabilizing rod and comprising two flat ramped portions within the upper linear slot that meet at an apex within the upper linear slot and between the two flat ramped upper linear slot portions; and a lower end integral with or physically connected to the spherical upper end, the lower end having one or more lower recesses configured to receive the first spinal rod or the second spinal rod, wherein the polyaxial link is operable to position the first stabilizing rod or the second stabilizing rod at a range of angles to the first spinal rod or the second spinal rod; and
wherein each monoaxial and polyaxial link is movably couplable to the first stabilizing rod or to the second stabilizing rod and is movably couplable to the first spinal rod fixed to the spine and to the second spinal rod fixed to the spine; and
stabilizing the spine at a desired spinal configuration;
wherein the stabilizer assembly is couplable to the first spinal rod and to the second spinal rod to stabilize the spine to prevent compression, distraction, or translation of the spinal cord during a spinal correction.

14. The method of claim 13, wherein the locking mechanism to lock the first rod-bearing leaf and the second rod-bearing leaf at the desired angle comprises one or more screws.

15. The method of claim 13, wherein the first stabilizing rod is coupled to the first rod-bearing leaf with a first threaded portion of the first stabilizing rod.

16. The method of claim 13, wherein the second stabilizing rod is coupled to the second rod-bearing leaf with a second threaded portion of the second stabilizing rod.

17. The method of claim 13, wherein each monoaxial or polyaxial link is movably coupled to the first stabilizing rod or to the second stabilizing rod with one or more adjustment nuts or one or more locking pins.

18. The method of claim 13, wherein each monoaxial or polyaxial link is movably couplable to the first spinal rod or to the second spinal rod at one or more components, each comprising a recess shaped to receive the first spinal rod or to the second spinal rod, and lockable in position with one or more screws.

19. The method of claim 13, wherein the first stabilizing rod is rotatably coupled to the first rod-bearing leaf to provide coronal or sagittal freedom of movement, or both, of the first stabilizing rod or the second stabilizing rod is rotatably coupled to the second rod-bearing leaf to provide coronal or sagittal freedom of movement, or both, of the second stabilizing rod; and wherein the first stabilizing rod has a locking mechanism to lock it at a desired position or the second stabilizing rod has a locking mechanism to lock it at a desired position.

20. The method of claim 13, wherein the first stabilizing rod or the second stabilizing rod is threaded and adjustment nuts are mounted on the first stabilizing rod or the second stabilizing rod to provide longitudinal freedom of movement or locking of one or more of the plurality of monoaxial or polyaxial links on the first stabilizing rod or the second stabilizing rod.

21. The method of claim 13, further comprising coupling the stabilizer assembly to at least one of the plurality of spinal rods oriented to allow the hinge to have coronal freedom of movement, sagittal freedom of movement, or a combination of coronal and sagittal freedom of movement.

* * * * *